US009522097B2

(12) United States Patent
Tennican

(10) Patent No.: US 9,522,097 B2
(45) Date of Patent: Dec. 20, 2016

(54) MIXING/ADMINISTRATION SYRINGE DEVICES, PROTECTIVE PACKAGING AND METHODS OF PROTECTING SYRINGE HANDLERS

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

(*) Notice: Subject to any disclaimer, the term of this patent is extended or adjusted under 35 U.S.C. 154(b) by 0 days.

(21) Appl. No.: 13/838,530

(22) Filed: Mar. 15, 2013

(65) Prior Publication Data

US 2013/0345626 A1    Dec. 26, 2013

Related U.S. Application Data

(63) Continuation-in-part of application No. 13/183,955, filed on Jul. 15, 2011, now Pat. No. 8,512,278, which
(Continued)

(51) Int. Cl.
*A61M 37/00* (2006.01)
*A61M 5/32* (2006.01)
(Continued)

(52) U.S. Cl.
CPC ............ *A61J 1/2096* (2013.01); *A61M 5/008* (2013.01); *A61J 1/10* (2013.01); *A61J 1/16* (2013.01);
(Continued)

(58) Field of Classification Search
CPC ............ A61M 2005/3117; A61M 2005/3128; A61M 5/002; A61M 5/008; A61M 5/31596; A61J 1/2096
(Continued)

(56) References Cited

U.S. PATENT DOCUMENTS 730,054 A    6/1903   Sheets
984,037 A    2/1911   Sheets
(Continued)

FOREIGN PATENT DOCUMENTS

CA    2513165 A1    8/2004
JP    01-131671     5/1989
(Continued)

OTHER PUBLICATIONS

EP 05807323 Search Report, Apr. 3, 2009, Hyprotek, Inc.
(Continued)

*Primary Examiner* — Rebecca E Eisenberg
(74) *Attorney, Agent, or Firm* — Wells St. John P.S.

(57) ABSTRACT

Medicant mixing/administration systems are provided that can include: a medicant vial; a syringe assembly comprising a barrel and a piston; a protective material supporting the syringe assembly and medicant vial; and a member within the system, the member separating the piston of the syringe assembly from the medicant vial. Systems are provided that can include: a syringe assembly comprising a barrel and a piston; having a forward end and an opposing back end; a protective material supporting the syringe assembly; and a needle housing coupled to the protective material. Medicant mixing/administration methods are also provided that can include, within a package, sufficiently clearing a restraining member from between a medicant vial and syringe plunger to pierce the medicant vial with a piercing structure coupled to the syringe plunger, the piercing providing medicant from the vial to the syringe assembly. Additional methods can include, upon opening a package containing a syringe assembly, extending a needle housing from the package.

7 Claims, 18 Drawing Sheets

Related U.S. Application Data is a continuation of application No. 12/242,121, filed on Sep. 30, 2008, now Pat. No. 8,002,737.

(60) Provisional application No. 60/977,557, filed on Oct. 4, 2007, provisional application No. 60/988,509, filed on Nov. 16, 2007, provisional application No. 61/082,870, filed on Jul. 23, 2008.

(51) Int. Cl.
*A61J 1/20* (2006.01)
*A61M 5/00* (2006.01)
*A61J 1/10* (2006.01)
*A61J 1/16* (2006.01)
*A61M 5/315* (2006.01)
*A61M 5/31* (2006.01)

(52) U.S. Cl.
CPC .............. *A61J 1/201* (2015.05); *A61J 1/2037* (2015.05); *A61J 1/2065* (2015.05); *A61M 5/002* (2013.01); *A61M 5/31596* (2013.01); *A61M 2005/3117* (2013.01); *A61M 2005/3128* (2013.01)

(58) Field of Classification Search
USPC ........ 206/365–366; 604/6.12, 187–188, 191, 604/194, 199, 240, 111, 89–92, 533
See application file for complete search history.

(56) References Cited

U.S. PATENT DOCUMENTS

| | | |
|---|---|---|
| 1,100,799 A | 6/1914 | Wedig |
| 1,465,793 A | 8/1923 | Schilling |
| 1,696,018 A | 12/1928 | Schellberg |
| 1,707,880 A | 4/1929 | Sheets |
| 2,453,590 A | 11/1948 | Poux |
| 2,540,461 A | 2/1951 | Smith |
| 2,555,878 A | 6/1951 | Drabicki |
| 2,661,740 A | 12/1953 | Hickey |
| 2,677,372 A | 5/1954 | Barnish |
| 2,693,186 A | 11/1954 | Ricker et al. |
| 2,818,999 A | 1/1958 | Miller |
| 2,842,124 A | 7/1958 | James |
| 2,869,544 A | 1/1959 | Ratcliff et al. |
| 3,052,239 A | 9/1962 | Silver et al. |
| 3,052,240 A | 9/1962 | Silver et al. |
| 3,164,303 A | 1/1965 | Trautmann |
| 3,342,180 A | 9/1967 | Sandhage et al. |
| 3,348,546 A | 10/1967 | Roberts et al. |
| 3,473,646 A | 10/1969 | Burke |
| 3,511,239 A | 5/1970 | Tuschhoff |
| 3,645,268 A | 2/1972 | Capote |
| 3,648,704 A | 3/1972 | Jackson |
| 3,659,602 A | 5/1972 | Cloyd |
| 3,841,329 A | 10/1974 | Killinger |
| 3,844,318 A | 10/1974 | Raia et al. |
| 3,938,520 A | 2/1976 | Scislowicz et al. |
| 3,946,732 A | 3/1976 | Hurscham |
| 4,014,330 A | 3/1977 | Genese |
| 4,031,892 A | 6/1977 | Hurschman |
| 4,044,757 A | 8/1977 | McWhorter et al. |
| 4,116,240 A | 9/1978 | Guiney |
| 4,142,633 A | 3/1979 | Raghavachari et al. |
| 4,153,057 A | 5/1979 | Kobel |
| 4,164,203 A | 8/1979 | Cavanagh |
| 4,166,533 A | 9/1979 | Maitland |
| 4,191,225 A | 3/1980 | Ogle |
| 4,244,364 A | 1/1981 | Grushkin |
| 4,303,069 A | 12/1981 | Cohen |
| 4,328,802 A | 5/1982 | Curley et al. |
| 4,405,317 A | 9/1983 | Case |
| 4,411,662 A | 10/1983 | Pearson |
| 4,424,057 A | 1/1984 | House |
| 4,464,174 A | 8/1984 | Ennis |
| 4,518,386 A | 5/1985 | Tartaglia |
| 4,585,446 A | 4/1986 | Kempf |
| 4,589,879 A | 5/1986 | Pearson |
| 4,591,357 A | 5/1986 | Sneider |
| 4,599,082 A | 7/1986 | Grimard |
| 4,624,667 A | 11/1986 | Rutnarak |
| 4,657,534 A | 4/1987 | Beck et al. |
| 4,660,569 A | 4/1987 | Etherington |
| 4,685,596 A | 8/1987 | Mattheis |
| 4,700,872 A | 10/1987 | Keyes et al. |
| 4,722,733 A | 2/1988 | Howson |
| 4,735,608 A | 4/1988 | Sardam |
| 4,758,231 A | 7/1988 | Haber et al. |
| 4,759,750 A | 7/1988 | DeVries et al. |
| 4,781,701 A | 11/1988 | Geprags |
| 4,838,855 A | 6/1989 | Lynn |
| 4,861,335 A | 8/1989 | Reynolds |
| 4,874,381 A | 10/1989 | Vetter |
| 4,886,495 A | 12/1989 | Reynolds |
| 4,898,209 A | 2/1990 | Zbed |
| 4,915,701 A | 4/1990 | Halkyard |
| 4,969,883 A | 11/1990 | Gilbert et al. |
| 4,994,029 A | 2/1991 | Rohrbough |
| 4,997,420 A | 3/1991 | Lefevre |
| 5,067,948 A | 11/1991 | Haber et al. |
| 5,069,670 A | 12/1991 | Vetter et al. |
| 5,080,649 A | 1/1992 | Vetter |
| 5,085,643 A | 2/1992 | Larkin et al. |
| 5,098,402 A | 3/1992 | Davis |
| 5,135,496 A | 8/1992 | Vetter et al. |
| 5,137,511 A | 8/1992 | Reynolds |
| 5,139,490 A | 8/1992 | Vetter et al. |
| 5,147,329 A | 9/1992 | Brannon |
| 5,171,214 A | 12/1992 | Kolber et al. |
| 5,181,909 A | 1/1993 | McFarlane |
| 5,226,900 A | 7/1993 | Bancsi et al. |
| 5,247,972 A | 9/1993 | Tetreault |
| 5,290,228 A | 3/1994 | Uemura et al. |
| 5,312,336 A | 5/1994 | Haber et al. |
| 5,320,603 A | 6/1994 | Vetter et al. |
| 5,330,426 A | 7/1994 | Kriesel et al. |
| 5,332,092 A | 7/1994 | Fischer |
| 5,334,163 A | 8/1994 | Sinnett |
| 5,356,375 A | 10/1994 | Higley |
| 5,356,380 A | 10/1994 | Hoekwater et al. |
| 5,364,369 A | 11/1994 | Reynolds |
| 5,372,586 A | 12/1994 | Haber et al. |
| 5,372,590 A | 12/1994 | Haber et al. |
| 5,393,497 A | 2/1995 | Haber et al. |
| 5,407,070 A | 4/1995 | Bascos et al. |
| 5,411,489 A | 5/1995 | Pagay et al. |
| 5,411,499 A | 5/1995 | Dudar et al. |
| 5,423,751 A | 6/1995 | Harrison et al. |
| 5,437,648 A | 8/1995 | Graves et al. |
| 5,466,219 A | 11/1995 | Lynn et al. |
| 5,466,220 A | 11/1995 | Brenneman |
| 5,470,327 A | 11/1995 | Helgren et al. |
| 5,472,403 A | 12/1995 | Cornacchia et al. |
| 5,478,314 A | 12/1995 | Malenchek |
| 5,478,337 A | 12/1995 | Okamoto et al. |
| 5,484,406 A | 1/1996 | Wong et al. |
| 5,489,266 A | 2/1996 | Grimard |
| 5,505,704 A | 4/1996 | Pawelka et al. |
| 5,529,189 A | 6/1996 | Feldschuh |
| 5,531,672 A | 7/1996 | Lynn |
| 5,531,683 A | 7/1996 | Kriesel et al. |
| 5,533,994 A | 7/1996 | Meyer |
| 5,549,569 A | 8/1996 | Lynn et al. |
| 5,566,729 A | 10/1996 | Grabenkort et al. |
| 5,569,191 A | 10/1996 | Meyer |
| 5,569,193 A | 10/1996 | Hofstetter et al. |
| 5,580,351 A | 12/1996 | Helgren et al. |
| 5,584,819 A | 12/1996 | Kopfer |
| 5,618,268 A | 4/1997 | Raines et al. |
| 5,630,800 A | 5/1997 | Blank et al. |
| 5,637,100 A | 6/1997 | Sudo |
| 5,647,845 A | 7/1997 | Haber et al. |
| 5,653,686 A | 8/1997 | Coulter et al. |

(56) References Cited

U.S. PATENT DOCUMENTS

| | | |
|---|---|---|
| 5,674,195 A | 10/1997 | Truthan |
| 5,685,866 A | 11/1997 | Lopez |
| 5,722,950 A | 3/1998 | Fujita et al. |
| 5,738,655 A | 4/1998 | Vallelunga et al. |
| 5,766,147 A | 6/1998 | Sancoff et al. |
| 5,769,825 A | 6/1998 | Lynn |
| 5,772,665 A | 6/1998 | Glad et al. |
| 5,776,125 A | 7/1998 | Dudar et al. |
| 5,785,701 A | 7/1998 | Sams et al. |
| 5,795,337 A | 8/1998 | Grimard |
| 5,807,323 A | 9/1998 | Kriesel et al. |
| 5,827,262 A | 10/1998 | Neftel et al. |
| 5,833,653 A | 11/1998 | Vetter et al. |
| 5,842,326 A | 12/1998 | Wolf |
| 5,897,527 A | 4/1999 | Tsukada |
| 5,928,215 A | 7/1999 | Caizza et al. |
| RE36,273 E | 8/1999 | Brannon |
| 5,951,160 A | 9/1999 | Ronk et al. |
| 5,976,115 A | 11/1999 | Parris et al. |
| 5,989,227 A | 11/1999 | Vetter et al. |
| 5,997,811 A | 12/1999 | Esposito |
| 6,027,472 A | 2/2000 | Kriesel et al. |
| 6,065,270 A | 5/2000 | Reinhard et al. |
| 6,099,511 A | 8/2000 | Devos et al. |
| 6,149,623 A | 11/2000 | Reynolds |
| 6,267,154 B1 | 7/2001 | Felicelli et al. |
| 6,280,430 B1 | 8/2001 | Neftel et al. |
| 6,319,225 B1 | 11/2001 | Sugita et al. |
| 6,349,850 B1 | 2/2002 | Cheikh |
| 6,358,236 B1 | 3/2002 | DeFoggi et al. |
| 6,364,866 B1 | 4/2002 | Furr et al. |
| 6,379,328 B1 | 4/2002 | Mac Clay |
| 6,379,340 B1 | 4/2002 | Zinger et al. |
| 6,391,014 B1 | 5/2002 | Silverman |
| 6,478,788 B1 | 11/2002 | Aneas |
| 6,478,808 B2 | 11/2002 | Nowakowski |
| 6,488,651 B1 | 12/2002 | Morris et al. |
| 6,491,665 B1 | 12/2002 | Vetter et al. |
| D472,316 S | 3/2003 | Douglas et al. |
| 6,527,738 B1 | 3/2003 | Jones et al. |
| 6,544,233 B1 | 4/2003 | Fukui et al. |
| 6,576,224 B1 | 6/2003 | Osbakken et al. |
| 6,591,876 B2 | 7/2003 | Safabash |
| 6,599,264 B1 | 7/2003 | Erni et al. |
| 6,599,273 B1 | 7/2003 | Lopez |
| 6,602,223 B2 | 8/2003 | Szapiro et al. |
| 6,626,309 B1 | 9/2003 | Jansen et al. |
| 6,638,244 B1 | 10/2003 | Reynolds |
| 6,650,929 B1 | 11/2003 | Nemoto et al. |
| 6,681,946 B1 | 1/2004 | Jansen et al. |
| 6,716,193 B1 | 4/2004 | Neftel |
| 6,729,370 B2 | 5/2004 | Norton et al. |
| 6,743,214 B2 | 6/2004 | Heil et al. |
| 6,802,828 B2 | 10/2004 | Reynolds |
| 6,808,511 B2 | 10/2004 | Pond |
| 6,817,987 B2 | 11/2004 | Vetter et al. |
| 6,852,103 B2 | 2/2005 | Fowles et al. |
| 6,912,800 B2 | 7/2005 | Vetter et al. |
| 7,036,288 B2 | 5/2006 | Vetter et al. |
| 7,074,216 B2 | 7/2006 | Fowles et al. |
| 7,077,835 B2 | 7/2006 | Robinson et al. |
| 7,081,109 B2 | 7/2006 | Tighe et al. |
| 7,134,782 B2 | 11/2006 | Coffeen et al. |
| 7,134,974 B2 | 11/2006 | Almasian et al. |
| 7,137,974 B2 | 11/2006 | Almasian et al. |
| 7,161,488 B2 | 1/2007 | Frasch |
| 7,213,702 B2 | 5/2007 | Takimoto et al. |
| 7,331,941 B2 | 2/2008 | Vetter et al. |
| 7,338,477 B2 | 3/2008 | Meyer et al. |
| 7,452,344 B2 | 11/2008 | Jorgensen et al. |
| 7,470,257 B2 | 12/2008 | Norton et al. |
| 7,470,258 B2 | 12/2008 | Barker et al. |
| 7,553,304 B2 | 6/2009 | Neftel |
| 7,563,245 B2 | 7/2009 | Mu |
| 7,708,719 B2 | 5/2010 | Wilmot et al. |
| 7,713,239 B2 | 5/2010 | Uber, III et al. |
| 7,731,678 B2 | 6/2010 | Tennican et al. |
| 7,736,353 B2 | 6/2010 | Reynolds |
| 7,753,891 B2 | 7/2010 | Tennican et al. |
| 7,824,373 B2 | 11/2010 | Kim et al. |
| 7,963,951 B2 | 6/2011 | Kitani et al. |
| 8,002,737 B2 | 8/2011 | Tennican |
| 8,137,307 B2 | 3/2012 | Tennican et al. |
| 8,197,459 B2 | 6/2012 | Jansen et al. |
| 2001/0016703 A1 | 8/2001 | Wironen et al. |
| 2002/0002354 A1 | 1/2002 | Vetter et al. |
| 2002/0022804 A1 | 2/2002 | Connolly et al. |
| 2002/0061281 A1 | 5/2002 | Osbakken et al. |
| 2002/0065490 A1 | 5/2002 | Heinz et al. |
| 2002/0068896 A1 | 6/2002 | Robinson et al. |
| 2002/0087118 A1 | 7/2002 | Reynolds et al. |
| 2003/0069545 A1 | 4/2003 | Arm |
| 2003/0114798 A1 | 6/2003 | Langley et al. |
| 2003/0225378 A1 | 12/2003 | Wilkie et al. |
| 2004/0122345 A1 | 6/2004 | Muller |
| 2004/0232171 A1 | 11/2004 | Bobst |
| 2005/0090797 A1 | 4/2005 | Almasian et al. |
| 2006/0027523 A1 | 2/2006 | Van Lintel et al. |
| 2006/0178642 A1 | 8/2006 | Gillespie et al. |
| 2006/0184103 A1 | 8/2006 | Paproski et al. |
| 2006/0275336 A1 | 12/2006 | Du Plessis |
| 2006/0278588 A1 | 12/2006 | Woodell-May |
| 2007/0249996 A1 | 10/2007 | Tennican et al. |
| 2008/0015496 A1 | 1/2008 | Hamedi-Sangsari |
| 2008/0319400 A1 | 12/2008 | Thorne, Jr. et al. |
| 2010/0114067 A1 | 5/2010 | Trieu et al. |
| 2010/0174268 A1 | 7/2010 | Wilmot et al. |

FOREIGN PATENT DOCUMENTS

| | | |
|---|---|---|
| JP | 3009662 | 1/1995 |
| WO | WO 96/29113 A | 9/1996 |
| WO | WO 99/37233 A1 | 7/1999 |
| WO | WO 99/45851 | 9/1999 |
| WO | WO 00/13723 A | 3/2000 |
| WO | WO 01/41666 A1 | 6/2001 |
| WO | WO 03/039632 | 5/2003 |
| WO | WO 2004/064706 A | 8/2004 |
| WO | WO 2005/049166 | 6/2005 |
| WO | WO 2006/044236 A2 | 4/2006 |

OTHER PUBLICATIONS

EP 13 18 2659 Search Report, Oct. 22, 2013, Hyprotek, Inc.
TW 094135759 Search Report, Nov. 25, 2011, Hyprotek, Inc.
EP 06839806 Search Report, Feb. 7, 2011, Hyprotek, Inc.
EP 08836593 Supp Search Report, Apr. 17 2012, Hyprotek, Inc.
PCT/US05/036071 IPRP, Jan. 26, 2007, Hyprotek, Inc.
U.S. Appl. No. 11/751,410, filed May 21, 2007, Tennican et al.
PCT/US05/036071 Search Report, Sep. 8, 2006, Hyprotek, Inc.
PCT/US05/036071Written Opinion, Sep. 8, 2006, Hyprotek, Inc.
PCT/US06/060745 IPRP, Jan. 26, 2011, Hyprotek, Inc.
PCT/US06/060745 Search Report, Apr. 11, 2008, Hyprotek, Inc.
PCT/US06/060745Written Opinion, Apr. 11, 2008, Hyprotek, Inc.
PCT/US08/078774 IPRP, Dec. 15, 2010, Hyprotek, Inc.
PCT/US08/078774 Search Report, Dec. 17, 2008, Hyprotek, Inc.
PCT/US08/078774Written Opinion, Dec. 17, 2008, Hyprotek, Inc.
TW 096103375 OfficeAction/SR, Nov. 12, 2012, Hyprotek, Inc.
Clip'n Ject [retrieved online Nov. 9, 2005]: http://www.westpharma.comiproducts/clip_n_Ject.asp?1=0.
Debioclip Manual [retrieved online Nov. 9, 2005]: http://www.debiotech.com/products/drugdd/debioclip.html.
http://www.duoject.com/flash/duoject.html (2 pages).
http://www.life-assist.com/setfinder/preslit.html; ICU Medical/Setfinder Needle Free Products, pp. 1-5.
PCT/US13/075069 Srch Rpt., Apr. 3, 2014, Search Report.
PCT/US13/075069 Wtn. Op., Apr. 3, 2014, Written Opinion.
TW 097138292 SR Translation, Jul. 31, 2014, Hyprotek, Inc.
PCT/US13/075069 IPRP, Jun. 16, 2015, Hyprotek, Inc.
EP 15191331.6, Search Report, Jun. 13, 2016, Hyprotek, Inc.

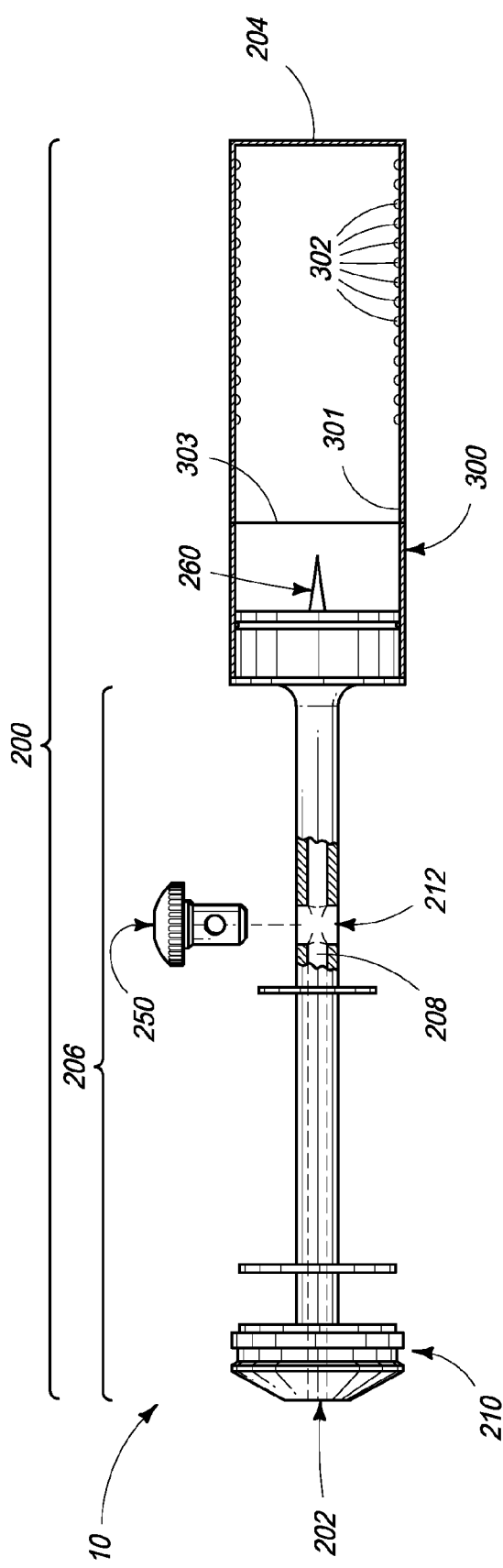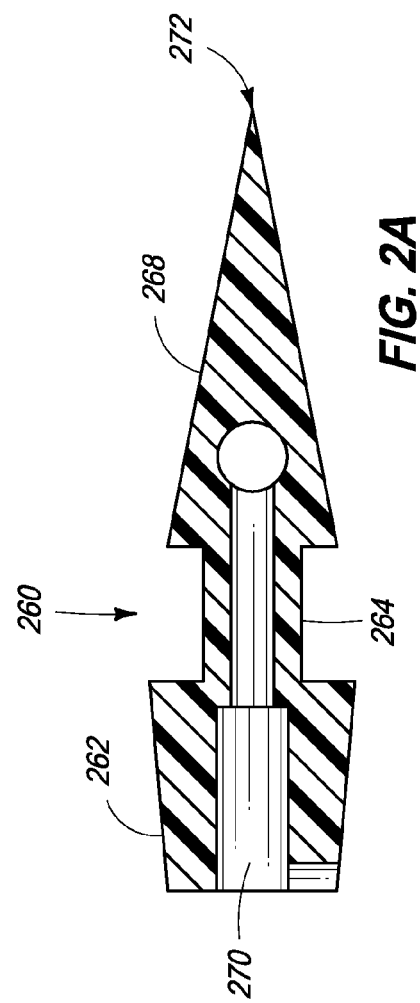
FIG. 2
FIG. 2A

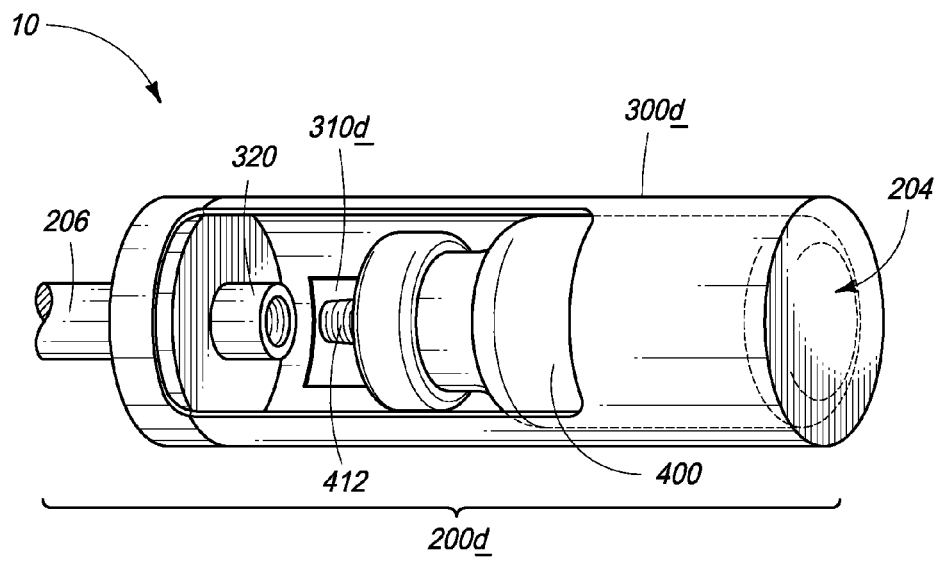
FIG. 7
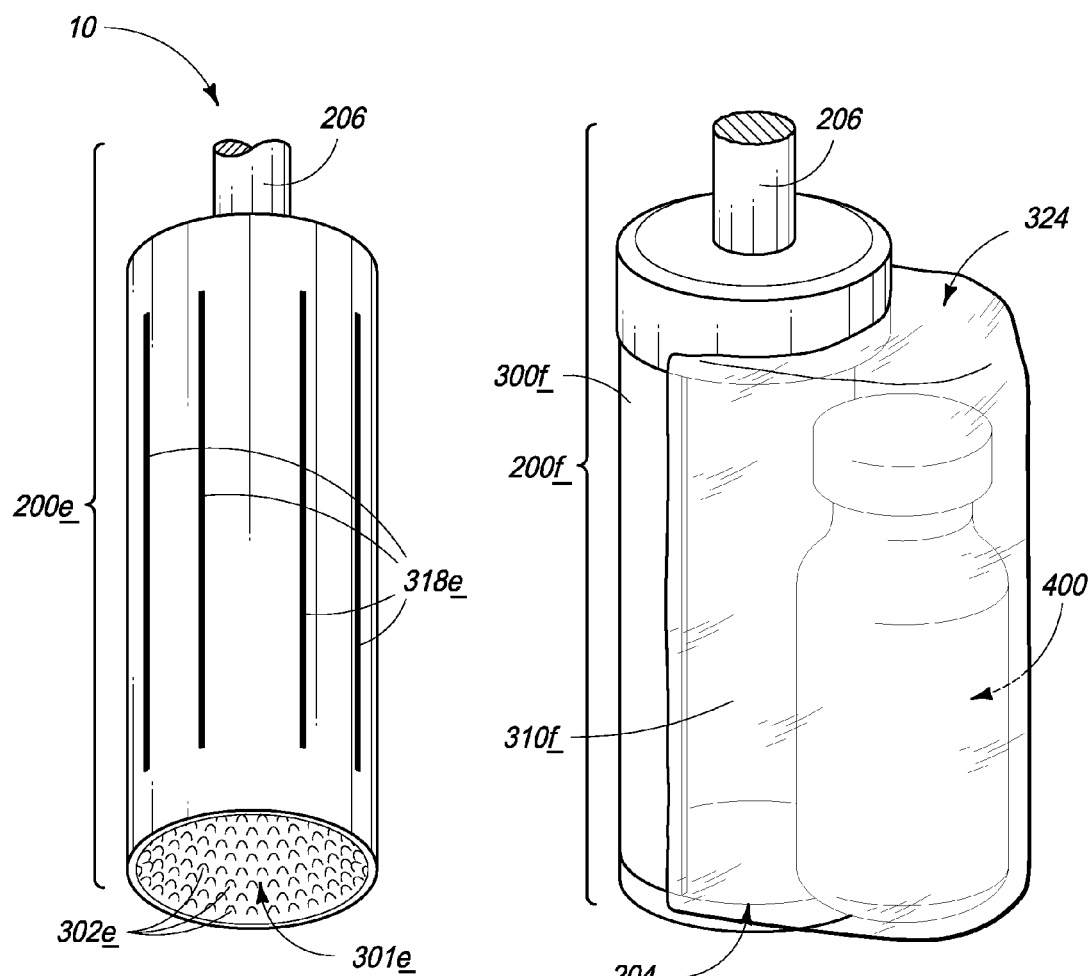
FIG. 8
FIG. 9

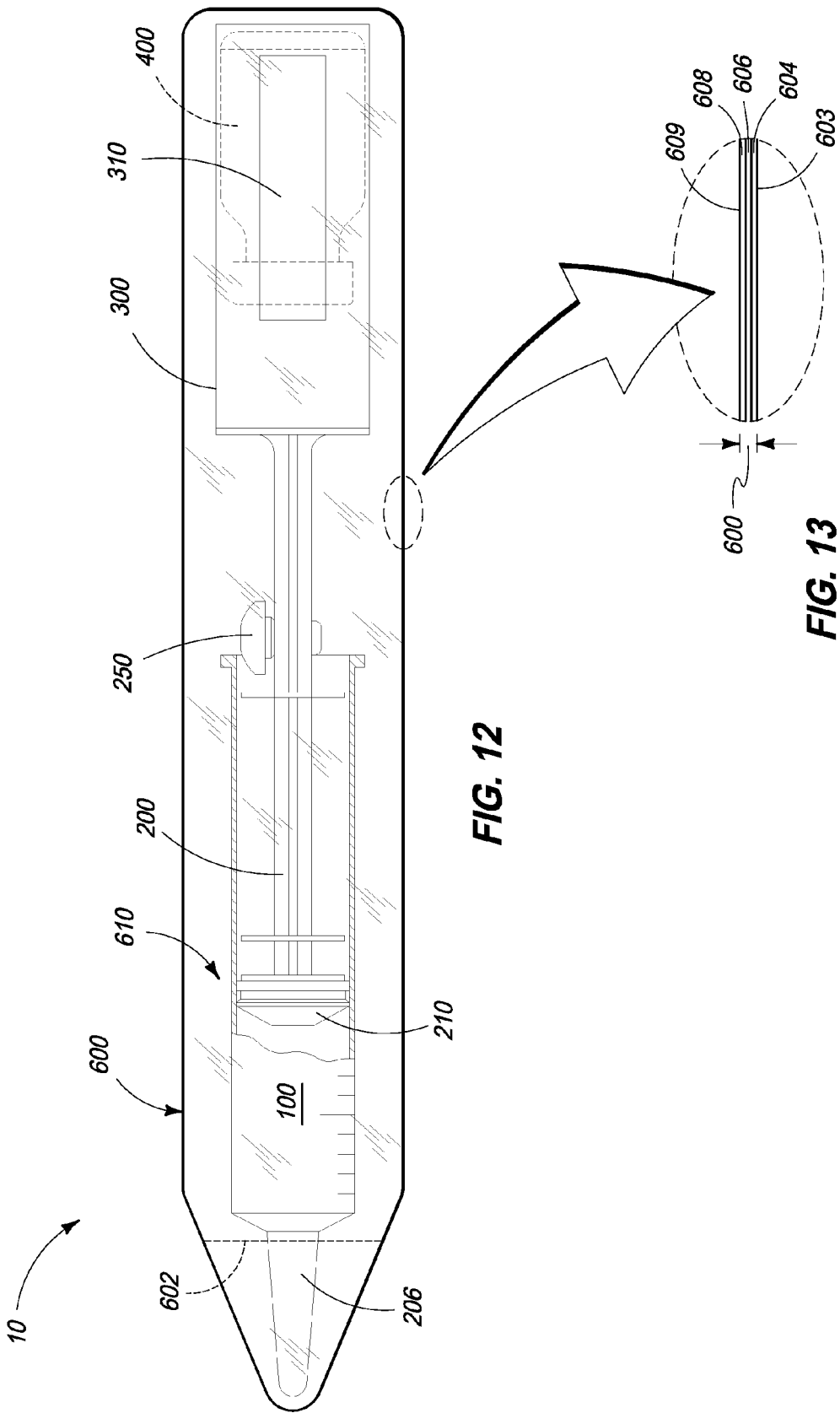

MIXING/ADMINISTRATION SYRINGE DEVICES, PROTECTIVE PACKAGING AND METHODS OF PROTECTING SYRINGE HANDLERS

RELATED PATENT DATA

This application is a continuation-in-part of U.S. patent application Ser. No. 13/183,955 filed Jul. 15, 2011, which is a continuation of U.S. patent application Ser. No. 12/242,121 filed Sep. 30, 2008, now U.S. Pat. No. 8,002,737 which issued Aug. 23, 2011, which claims priority under 35 U.S.C. §119 to Provisional Patent Application No. 60/977,557, which was filed Oct. 4, 2007; and to Provisional Patent Application No. 60/988,509, which was filed Nov. 16, 2007; and to Provisional Patent Application No. 61/082,870, which was filed Jul. 23, 2008, the entirety of each of which are incorporated herein by reference.

TECHNICAL FIELD

The invention encompasses syringe devices, mixing administration systems, protective packaging for syringe devices and components, and methods of protecting syringe device handlers from contents of those devices.

BACKGROUND OF THE INVENTION

Preparation of medicants or medication agents and administration of such agents to an individual often involves mixing of two or more components to form the agent and subsequent delivery of the mixed medicant to the individual. The mixing of components can typically involve extraction of one component in fluid form from a vial or other container and transfer of such components into a separate container which holds another component. In particular instances, only a portion of the contents of a vial or container is to be utilized for preparing a mixture prior to administering. Accordingly, the extraction and transfer can involve precise measuring of one or more components to be mixed.

A variety of problems may occur when utilizing conventional methodology and devices for mixing and/or administering medicants to an individual. For example, where multiple components are to be mixed, extraction and transfer of one component and introduction of such component into another component can potentially expose one or both of the components to a non-sterile or contaminated environment leading to contamination of the resulting medicant. Additionally, incomplete extraction or improper measurement of one or more components can result in preparation and/or administration of an improper dosage. In particular instances, once a medicant is mixed the mixture must again be extracted from a vial or container into a syringe prior to administering to an individual. Such additional transfer can lead to additional opportunities for contamination, incomplete extraction of contents and/or inaccurate measuring of a component or the resulting medicant.

In practice, there is limited availability of sterile environments for maintaining sterility during transfer and/or mixing of components, or preparation and transfer of medicants. Additional errors can result from use of the wrong diluent to reconstitute the medication. Preparation of medicants utilizing multiple components can be tedious and time consuming due to factors such as the need to access individually packaged items such as separate vials and/or transfer devices, or to measure one or more components to be combined to form the medicant.

Another factor to be considered when preparing medicants for administration is the nature of the medicants contained in the device and/or device components. For example, agents contained within device components may be potentially harmful to handlers upon exposure. Such potentially harmful agents include but are not limited to allergens, teratogens, endocrine-disruptors, carcinogens, or otherwise toxic or potentially toxic materials. Many conventional medicant administration devices potentially expose the handler of such device to the medicants being administered or prepared during the preparation and administration processes.

It would be desirable to develop alternative methodology and systems for preparation and administration of medicants and systems to protect handlers from exposure to contents of medicant device components.

SUMMARY OF THE INVENTION

In one aspect the invention includes a syringe device mixing/administration system including a syringe barrel having a forward end and an opposing back end. The system further includes a syringe piston insertable into the back end of the syringe barrel and a fluid bag reversibly attached to the forward end of the syringe barrel. A protective film material encases the syringe barrel, the syringe piston and the fluid bag.

In one aspect the invention includes a syringe device having a syringe barrel with an internal chamber and a syringe piston having a first end insertable into the internal chamber, a second end and a stem extending from the first end to a container housing. The container housing extends to the second end of the syringe piston and is configured to house a container. At least a portion of the container housing is insertable within the internal chamber of the syringe barrel. A fluid passageway extends from the container housing through the piston stem and through the first end of the piston.

In one aspect the invention includes a method of protecting a syringe handler including providing the components of a syringe device and encasing the components in a protective film. The protective film includes one or more members of the group consisting of polypropylene (PP), polyvinyls, aluminum foil, aluminum oxide coated nylon, biaxially oriented (biax) nylon (BO nylon), biax polyethylene terephthalate (BOPET), aluminum oxide coated BOPET, polycarbonate, oriented polypropylene (OPP), biax OPP (BOPP), high density polyethylene (HDPE), medium density polyethylene (MDPE), low density polyethylene (LDPE), linear low density polyethylene (LLDPE), ethylene vinyl acetate copolymer (EVA), metallocene, ionomer, polyvinylidene chloride (PVdC), metallized PET, metallized OPP, poly(ethylene vinyl alcohol) (EVOH), coex, surlyn, silicon oxide coated BOPET, and paper. The protective film packaging can be referred to as "active" meaning it allows manipulation of the contained device components without opening of the packaging. In one embodiment the packaging film is loose to allow manipulation of the syringe components relative to one another without opening or puncturing the film.

In one aspect the invention includes a method of protecting a syringe handler including providing the components of a syringe device, encasing the components in a protective film comprising one or more members of the group consisting of polypropylene (PP), polyvinyls, aluminum foil, aluminum oxide coated nylon, biaxially oriented (biax) nylon (BO nylon), biax polyethylene terephthalate (BOPET), aluminum oxide coated BOPET, polycarbonate, oriented polypropylene (OPP), biax OPP (BOPP), high density polyethylene (HDPE), medium density polyethylene (MDPE), low density polyethylene (LDPE), linear low density polyethylene (LLDPE), ethylene vinyl acetate copolymer (EVA), metallocene, ionomer, polyvinylidene chloride (PVdC), metallized PET, metallized OPP, poly(ethylene vinyl alcohol) (EVOH), coex, surlyn, silicon oxide coated BOPET, and paper. The protective film is formed to at least partially conform to the shape of the components. The protective film is heat sealed to at least some of the components of the syringe device.

In one aspect the invention includes protective syringe device packaging that includes a laminate film of material sealed to encase the components of a syringe device containing a potentially harmful agent where the laminate film includes at least one member of the group consisting of polypropylene (PP), polyvinyls, aluminum foil, aluminum oxide coated nylon, biaxially oriented (biax) nylon (BO nylon), biax polyethylene terephthalate (BOPET), aluminum oxide coated BOPET, polycarbonate, oriented polypropylene (OPP), biax OPP (BOPP), high density polyethylene (HDPE), medium density polyethylene (MDPE), low density polyethylene (LDPE), linear low density polyethylene (LLDPE), ethylene vinyl acetate copolymer (EVA), metallocene, ionomer, polyvinylidene chloride (PVdC), metallized PET, metallized OPP, poly(ethylene vinyl alcohol) (EVOH), coex, surlyn, silicon oxide coated BOPET, and paper.

In accordance with example implementations, medicant mixing/administration systems are provided that can include: a medicant vial; a syringe assembly comprising a barrel and a piston; a protective material supporting the syringe assembly and medicant vial; and a member within the system, the member separating the piston of the syringe assembly from the medicant vial.

According to other example implementations, medicant mixing/administration systems are provided that can include: a syringe assembly comprising a barrel and a piston; having a forward end and an opposing back end; a protective material supporting the syringe assembly; and a needle housing coupled to the protective material.

A medicant mixing/administration method are also provided with the methods including, within a package, sufficiently clearing a restraining member from between a medicant vial and syringe plunger to pierce the medicant vial with a piercing structure coupled to the syringe plunger, the piercing providing medicant from the vial to the syringe assembly.

Additional methods can include, upon opening a package containing a syringe assembly, extending a needle housing from the package.

BRIEF DESCRIPTION OF THE DRAWINGS

Preferred embodiments of the invention are described below with reference to the following accompanying drawings.

FIG. 2 illustrates the piston portion of the syringe device illustrated in FIG. 1 in partial cross-sectional view with FIG. 2A showing an enlarged view of a piercing structure in accordance with one aspect of the invention.

FIG. 7 shows a partially cut away view of an additional alternative embodiment of a piston configuration in accordance with another aspect of the invention.

FIG. 8 shows an additional alternative embodiment of a piston configuration in accordance with another aspect of the invention.

FIG. 9 shows an additional alternative piston configuration in accordance with an additional aspect of the invention.

FIG. 12 illustrates a mixing administration system in accordance with another aspect of the invention where the system includes protective packaging.

FIG. 13 is a fragmentary cross-sectional side view of a portion of the protective packaging illustrated in FIG. 12.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In general aspects, the invention pertains to systems utilized for mixing and/or administering medicants. Devices, components of devices, packaging, and methods of mixing and/or administration are encompassed by the invention and are depicted and described herein.

The components and methods described and exemplified herein can be utilized in conjunction with many of the devices and methods described in U.S. patent application Ser. Nos. 11/238,880 and 11/558,146, hereby incorporated by reference. It is to be understood that many of the concepts of the present invention can be utilized in conjunction with, or can be adapted to, other device configurations including conventional syringe devices and components, and those yet to be developed.

Syringe devices and other devices of the invention are not limited to particular sizes and can vary depending upon the volume of medicant to be mixed and/or administered. Accordingly, it is to be understood that the accompanying drawings are for illustrative purposes only and are not meant to limit the devices to any particular size or volumes.

Figure 1:
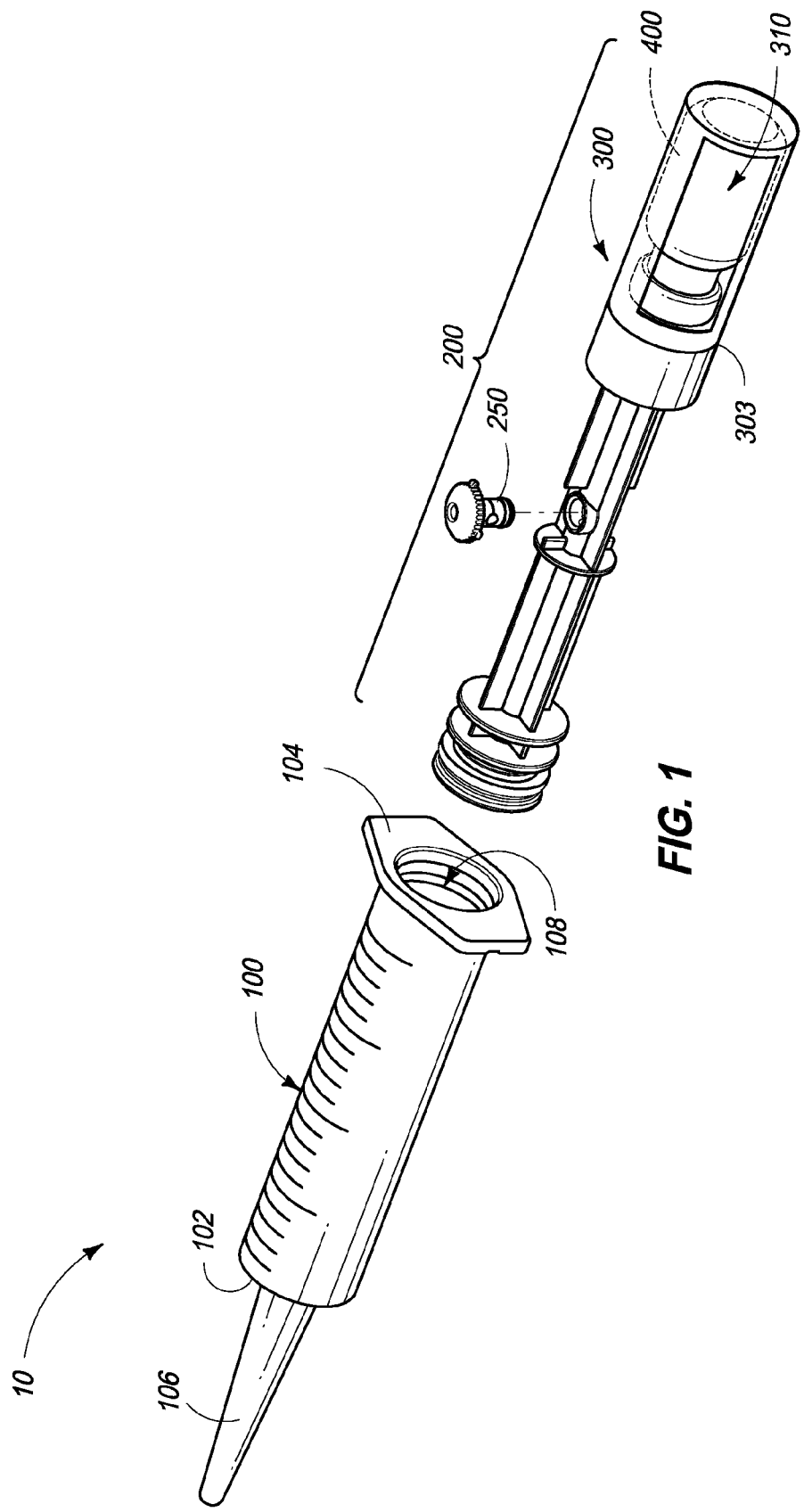
FIG. 1 diagrammatically illustrates a syringe mixing/administration system in accordance with one aspect of the invention.

Referring initially to FIG. 1, a syringe device for mixing and administrating a medicant is illustrated in accordance with one aspect of the invention. Mixing administration system 10 includes a syringe barrel 100 having a first end 102 and an opposing second end 104. First end 102 can be configured to reversibly attach to a needle or other medical equipment. Such reversible attachment can be, for example, a twist-type fitting such as a LUER-LOK® fitting, or an alternative type fitting. A cap 106 can be provided to cover an opening at first end 102 or to cover a needle disposed at first end 102. Syringe barrel 100 can be described as having an internal chamber 108.

Mixing administration system 10 further includes a piston 200 that is insertable into the internal chamber 108 of syringe barrel 100 through second end 104 as depicted in FIG. 1. In the configuration shown, piston 200 includes a valve 250 and a container housing 300 having an opening 310 and which houses a container such as a vial 400 as illustrated. It is noted that housing 300 completely encases vial 400 providing an enclosed compartment with the exception of opening 310. The outer diameter of housing 300 is such that housing 300 can be inserted within chamber 108 of syringe 100.

Piston 200 of FIG. 1 is shown in greater detail in FIG. 2. Piston 200 has a first end 202 and an opposing second end 204 and a stem portion 206 which extends from first end 202 to container housing 300. Container housing 300 extends from the piston stem to the second end 204 of the piston. Piston stem 206 has an internal fluid passage 208 which extends longitudinally from first end 202 to piston housing 204. A piercing structure 260 is provided in association with piston stem 206.

An enlarged view of piercing structure 260 is shown in cross-section in FIG. 2A. Piercing structure 260 can have a base portion 262, a head portion 268 having a tip 272, and a stem portion 264 extending between the base and the head. A fluid channel 270 runs longitudinally centrally through the base portion and the stem and emerges from a side of the head portion of the piercing device at a location other than tip 272. This configuration allows piercing of a septum to occur without coring. The shape of the piercing device allows the septum to be retained across the stem portion and assists in retaining the vial from pulling back off the device after piercing has occurred.

Fluid passage through piston stem 206 and the piercing device is controlled by way of valve 250, which is insertable into an opening 212 in stem portion 206 across fluid passageway 208.

Vial housing 300 is shown in cross-section in FIG. 2 to illustrate internal features. Housing 300 has internal sidewalls 301 which can be textured by, for example, providing raised features such as raised bumps 302 along at least a portion of such sidewalls. Although raised features 302 are shown as bumps it is to be understood that alternative raised features can be utilized such as ridges, ribs, etc. Texturing in sidewalls 301 can assist in providing a tight fit between the sidewalls of housing 300 and a container or vial provided within the housing and help retain the positioning of such container within the housing. Further, the thickness of the housing walls can be such to provide a tight fit with the container (i.e. have an inner diameter only slightly larger than the largest outer diameter of the enclosed container), and be thin enough to allow the housing to fit within the syringe chamber.

Housing 300 is depicted in FIGS. 1 and 2 as comprising a two-part housing having a seam or seal 303 between the two portions of the housing. The relative lengths of the two portions of housing 300 is for illustrative purposes only and the positioning of seam 303 can be anywhere along the length of the housing or alternatively can be a longitudinal seam running lengthwise along the housing (not shown). Alternatively, vial housing 300 can comprise a cap and an insert portion so long as the largest outer diameter of housing 300 can insert within the chamber barrel.

Referring again to FIG. 1, syringe system 10 can be provided in an initial "pre-mixed" condition where a first medicant component is provided within syringe barrel 100 and a second medicant component is provided within the container or vial 400 within chamber housing 300. In its initial state, syringe system 10 is provided to have a portion of syringe piston 200 including piston seal 210 inserted within chamber 108 and valve 250 provided in a closed state blocking fluid passage through piston stem 206. This configuration is depicted in FIG. 12. In this initial configuration vial 400 is positioned against the back of the housing at second end 204 of the piston stem. The textured sidewalls of housing 300 can help retain vial 400 in its initial position.

When mixing is desired, vial 400 can be manipulated via access through opening 310 in housing 300 and can be slid forward toward first end 202 of piston 200. Such sliding can bring vial 400 into contact with piercing structure 260 and, using sufficient force, can allow piercing of a septum of the vial by the piercing structure to establish fluid communication between the fluid channel 270 through piercing structure 260 and the vial. Once the piercing structure is engaged across the septum, the shape of the piercing structure along with the textured sidewalls assists in maintaining the positioning of the vial in the forward position within the housing.

Once fluid communication has been established between the vial and the fluid passageway, valve 250 can be repositioned to an "on" position to allow fluid communication between the vial and the syringe barrel. Piston 200 can then be slid forward into syringe barrel 100 to cause fluid transfer between chamber 108 and vial 400. Repeated forward and backward sliding motion of the piston can be utilized to mix the two components. Such mixing can be further assisted by, for example, shaking, agitating and/or swirling of the syringe system.

When sufficient mixing has occurred, the mixed medicant can be drawn into syringe chamber 108 by withdrawing syringe piston 200 to its original position. Valve 250 is then repositioned to the "closed" position to block fluid communication between syringe chamber 108 and vial housing 400. When administration is desired cap 106 can be removed to expose a needle or appropriate attachment fitting for injection by needle, IV port, etc. Administration is achieved by sliding piston 200 forward into syringe barrel 108.

Figure 3:
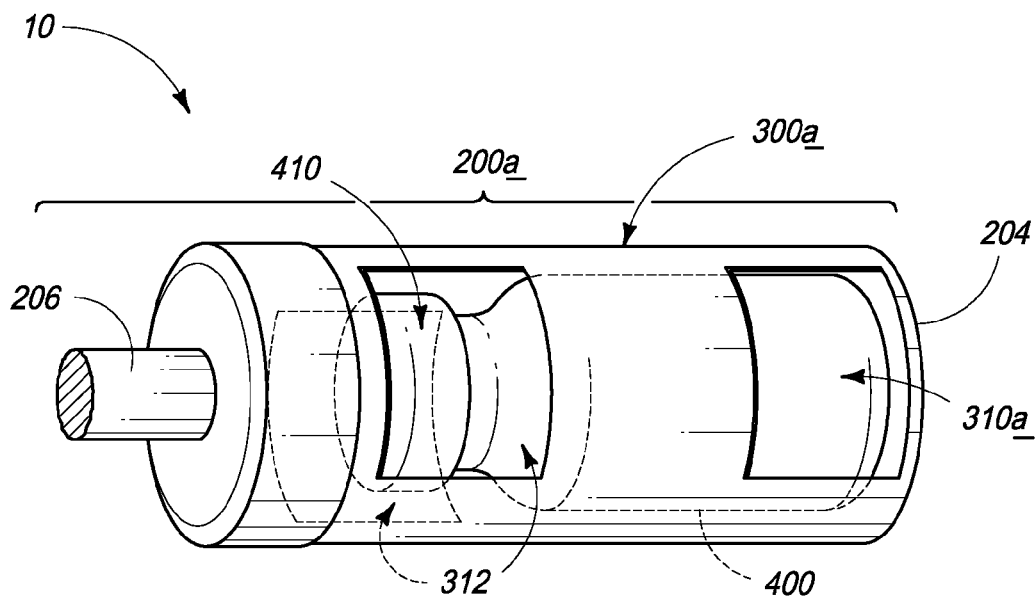
FIG. 3 illustrates an alternate embodiment of a piston configuration in accordance with another aspect of the invention.

Referring next to FIG. 3, such depicts an alternative syringe housing configuration relative to those discussed above with reference to FIG. 2. Features identical to those above with respect to FIG. 2 are numbered identically. Features analogous to those above with respect to FIG. 2 are given the same numeric identifier with an appended "a". New features are assigned new numeric identifiers. In particular instances, container or vial 400 can be provided with a metal end or plastic cap 410. Vial housing 300a can be provided to have one or more openings 312 to allow access to vial cap 410 for removal of such cap prior to repositioning of the vial within the chamber housing. The shape of openings 312 is not limited to the rectangular openings shown. Such openings can be, for example, round, oval or other appropriate shape. Preferably, openings 312 are sufficiently large to allow extraction of cap 410 from within chamber housing 300a.

Once cap 410 has been removed from housing 300a, vial 400 can be slid forward onto the piercing structure via access opening 310a. As illustrated by FIG. 3 as compared to FIG. 2, access-opening 310/310a is not limited to a particular length or width so long as sufficient space is provided for manipulation of vial 400 within housing 300a. Vial housing 300a (and subsequently discussed vial housings) can comprise textured sidewalls as discussed above with respect to FIG. 2.

Figure 4:
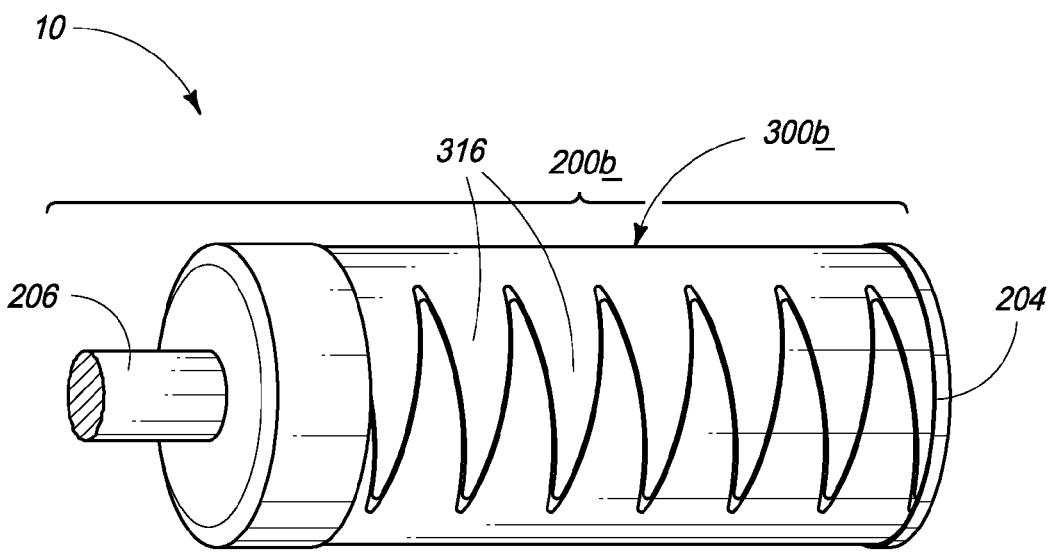
FIG. 4 shows an additional alternative embodiment of a piston configuration in accordance with another aspect of the invention.

FIG. 4 depicts an additional alternative housing configuration. Analogous features relative to those discussed above are assigned analogous numeric identifiers with an appended "b". New features are assigned new numeric identifiers. Housing 300b depicted in FIG. 4 can be configured to comprise a series of spaced intertwined "fingers" of material 316. Such spaced intertwined fingers leave openings or slits there-between and are flexible enough to allow access to and manipulation of vial 400 within housing 300b. Such fingers are movable relative to one another and can be bent slightly outward relative to housing 300b to allow insertion of a finger or tool device to slide vial 400 forward within housing 300b. Further, in the case where vial 400 has a plastic or metal lid, such lid can be removed between fingers 316.

The shape and spacing of fingers 316 is not limited to the triangular close-fit shown. For example, fingers 316 can be spaced and/or can be alternatively shaped such as rectangular, rounded, etc.

Figure 5:
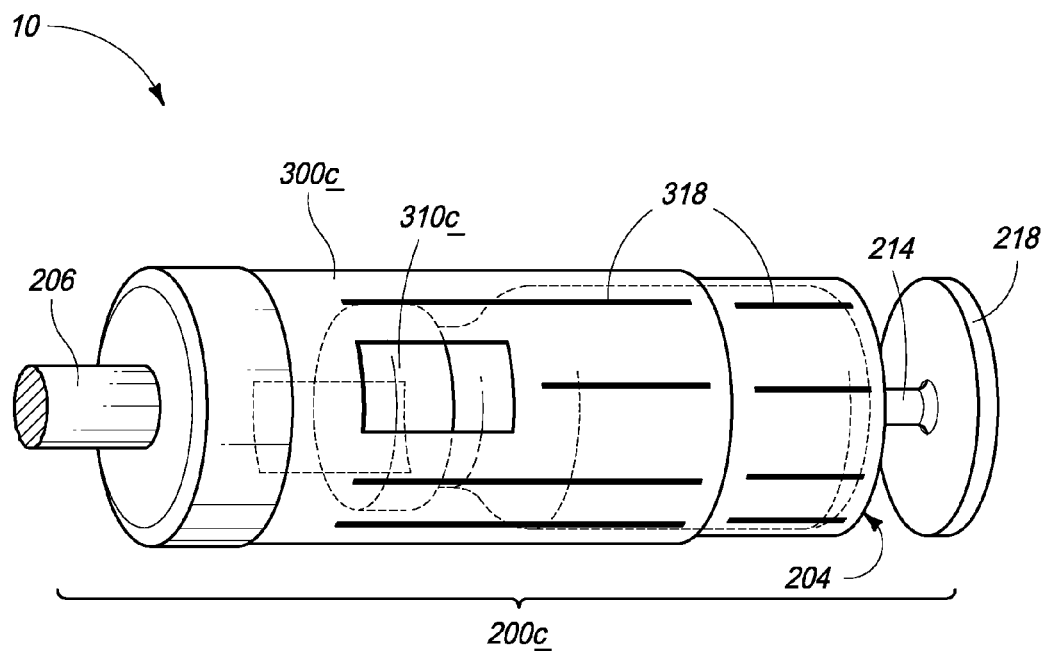
FIG. 5 shows an additional alternative embodiment of a piston configuration in accordance with another aspect of the invention.

Additional aspects of housing configurations are represented in FIG. 5. It is noted with reference to FIG. 5 that the positioning of opening 310c is not limited to a specific location. For example, opening 310c can be positioned proximate the neck of vial 400 to allow vial 400 to be slid forward within housing 300c by asserting a forward pressure beneath the vial head or lip area above the neck. FIG. 5 additionally illustrates a housing configuration where the internal housing fits snugly against the sidewalls of vial 400. To allow manipulation of vial 400 within the housing, one or more slits 318 can be provided lengthwise through the housing to allow a slight expansion of the housing. The number and length of slits 318 is not limited to a particular value.

Figure 6:
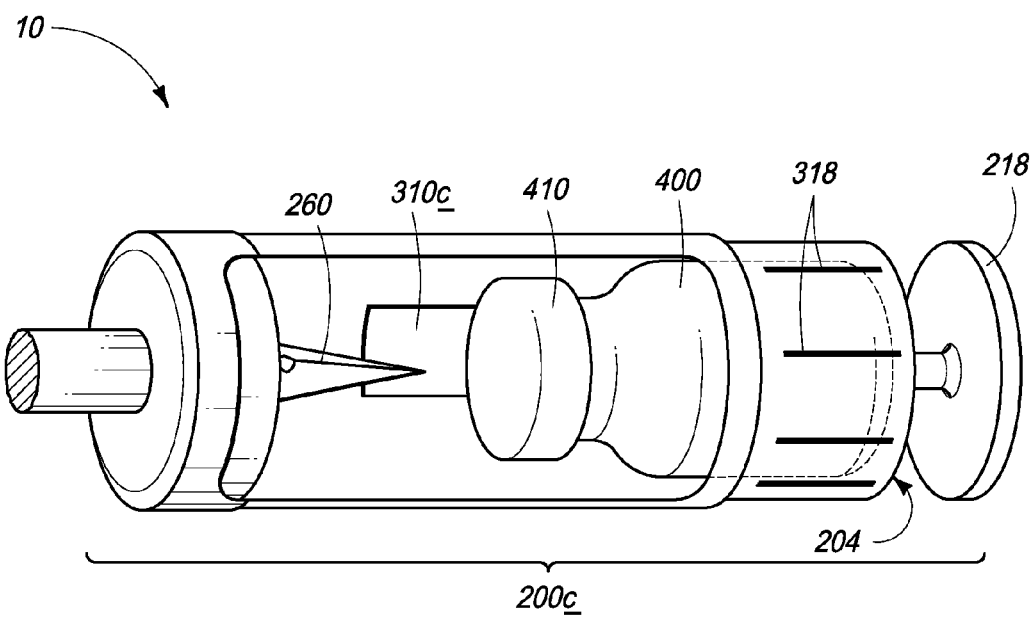
FIG. 6 shows the piston configuration of FIG. 5 showing a partially cut away view.

FIG. 5 additionally illustrates an extension from second end 204 of piston 200c comprising a stem portion 214 and a disc portion 218. Such extension can allow adaptation of syringe device 10 for use in a syringe pump. FIG. 6 shows a partial cut away view of the housing depicted in FIG. 5. As illustrated in FIG. 6, an opposing opening 310 can be provided to assist in manipulating vial 400 within the housing. Such manipulation can include piercing of a septum with piercing device 260 and can optionally include removal of a metal and/or plastic lid 410 from vial 400.

A partial cut away view of an alternative configuration is depicted in FIG. 7. In particular instances vial or container 400 can include a twist type fitting such as a LUER-LOK® fitting 412 rather than a septum. Accordingly, housing 300d can be configured to have a corresponding receiving fitting 320 configured to receive twist type fitting 412. Manipulation of vial 400 within housing 300d can therefore include turning of vial 400 to twist fitting 412 into receiving fitting 320 utilizing access openings 310d.

Referring next to FIG. 8, such depicts an alternative housing 300e having an open bottom at second end 204 of piston 200e. As illustrated, housing 300e can have surface texture features 302e along internal sidewalls 301e and can additionally optionally include expansion slits 318e as described above. Such housing can allow a vial/container to be inserted having a tight fit with the inner sidewalls 301e of the chamber housing, yet allow such container to be repositioned by forward pressure on the bottom of the container. Where the container has a metal and/or plastic cap, one or more access holes (not shown) can be provided along the housing to allow extraction of such lid, or the lid can be removed prior of insertion of the container into the housing.

Referring next to FIG. 9, such shows an alternative embodiment of a syringe housing 300f having an expanded opening 310f large enough for insertion and removal of a container/vial 400. Embodiment 300f additionally includes a vial/container shield 324 which can be, for example, a preferably clear plastic material such as a bag or pouch type material. Shield 324 can be attached to housing 300f and is preferably attached to completely encompass opening 310f as well as the vial/container. Shield 324 is provided to be flexible enough to allow manipulation of vial 400 including removal of any plastic and/or metal lid from the container and insertion of container 400 into the housing 300f. Further manipulation of the container can include sliding the container forward within housing 300f to engage the piercing structure across a septum of the container or attach the container via an alternative fitting.

Figure 10:
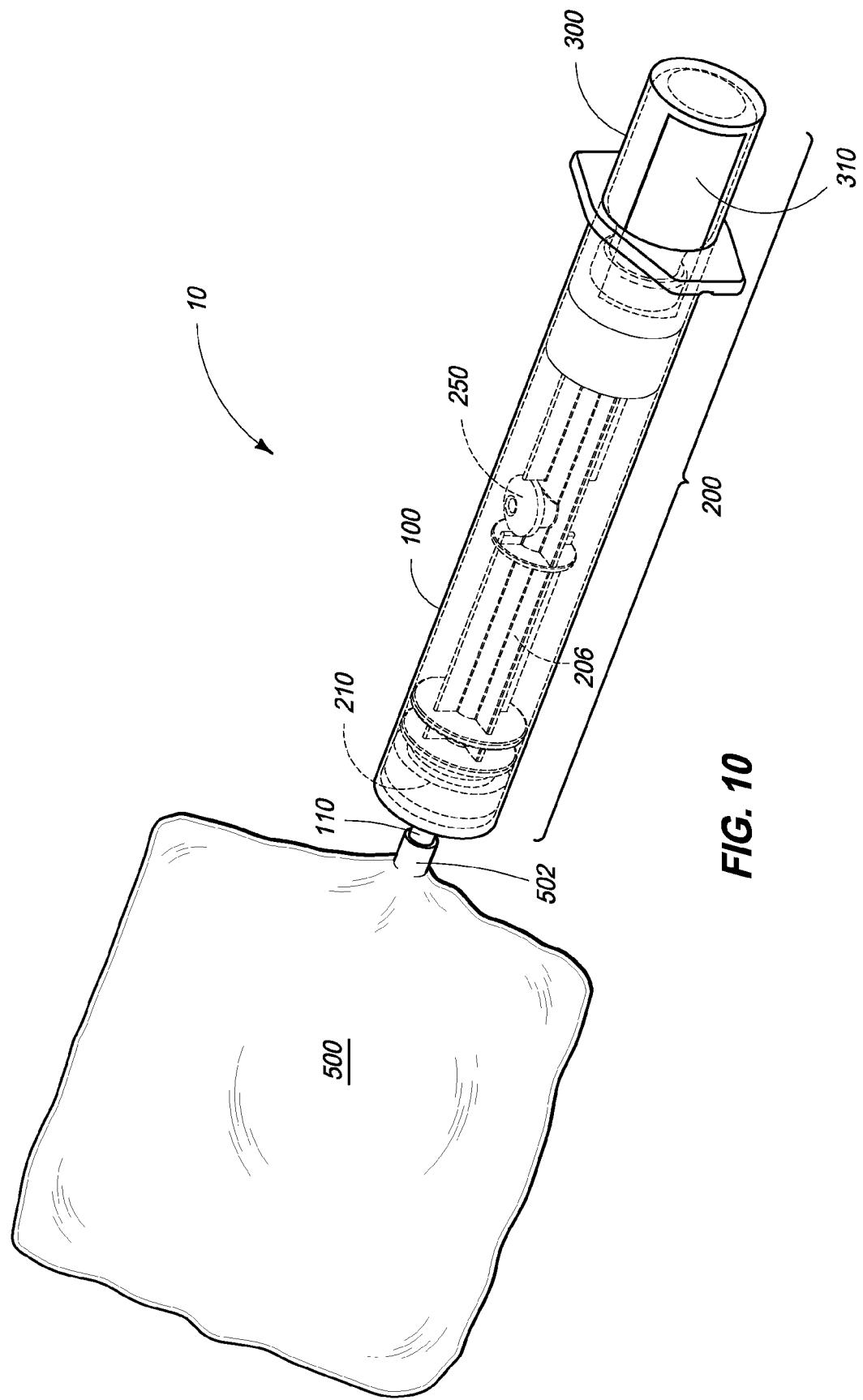
FIG. 10 illustrates an alternative mixing administration system configuration in accordance with another aspect of the invention.

An alternative embodiment of a syringe mixing/administration system is depicted in FIG. 10. Syringe device 10 can comprise, for example, a syringe barrel component 100 and a piston component 200 such as those described above with reference to FIG. 1. Housing component 300 can be as described with reference to any of the figures previously described. Alternatively, system 10 can comprise a syringe device as described in one of applicant's earlier filed applications which are incorporated by reference (see above). Syringe device 10 further includes a medicant bag 500 which can be reversibly attached to syringe barrel 100. Where syringe barrel 100 comprises a LUER-LOK® or other twist type fitting 110, bag 500 can be configured to comprise a corresponding opposing receiving twist type fitting 502. Where fitting 110 is an alternative type fitting, bag fitting 502 can be configured to form fit to fitting 110.

Medicant bag 500 is a bag for containing fluids and can therefore be referred to as a fluid bag. The fluid bag can be provided in an initially empty state or having an initial fluid content.

Where fluid bag 500 is provided initially containing a medicant fluid or diluent, syringe device 10 can be provided in an initial configuration having syringe piston 200 positioned such that stopper 210 is at the forward end of syringe barrel 100. Partial withdrawal of the piston can be utilized to extract fluid from bag 500 into syringe barrel 100. A vial disposed within housing 300 can be slid forward onto piercing structure (or alternate connecting structure) and valve 250 can be repositioned to an "on" position to establish fluid communication between the syringe barrel and the enclosed vial. Mixing can occur by insertion and withdrawal of the syringe piston into the syringe barrel. Syringe barrel 100 can then be removed from bag 500 in preparation for administration of the mixed medicant.

Figure 11:
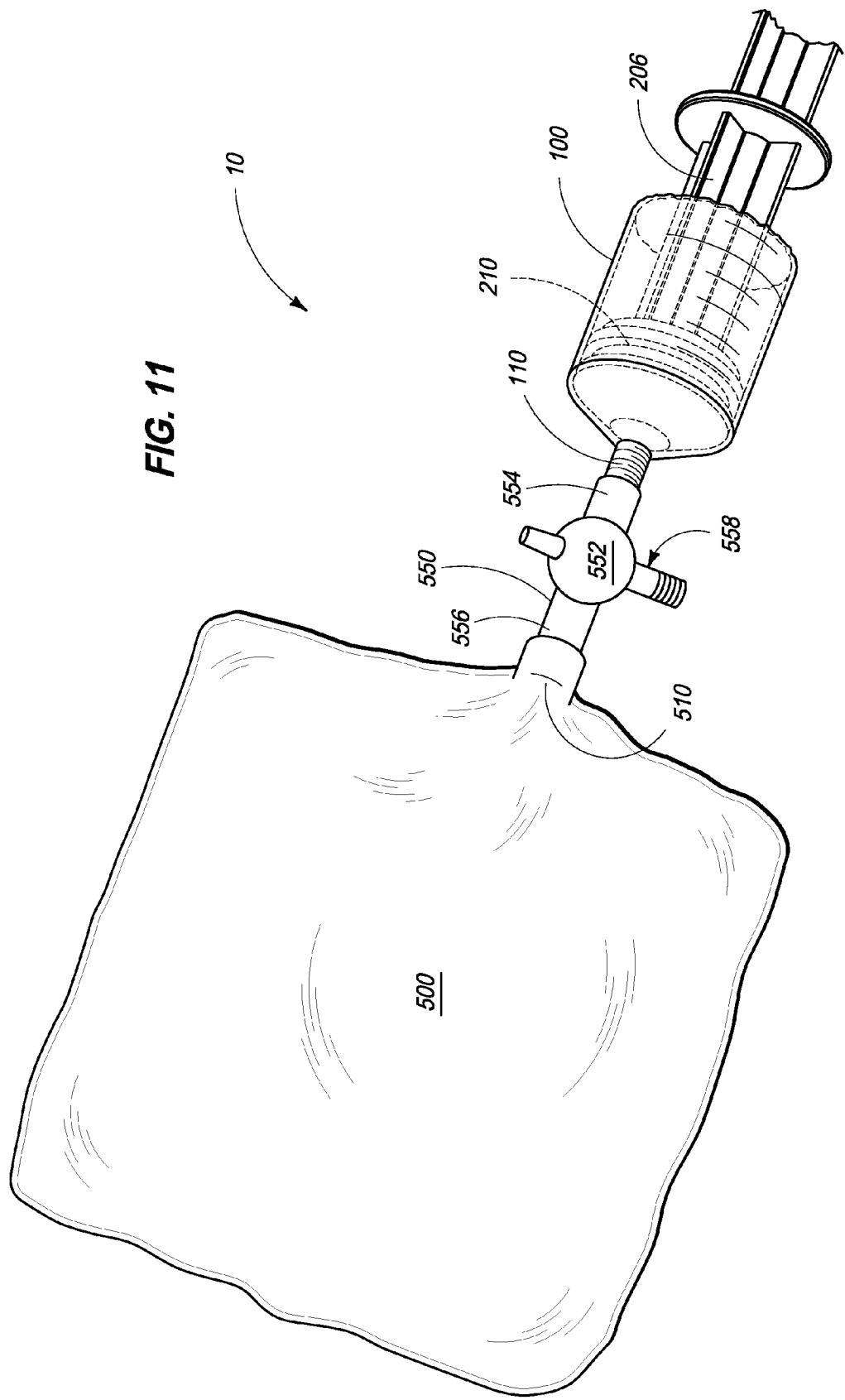
FIG. 11 illustrates an additional embodiment of a syringe mixing/administration system in accordance with another aspect of the invention.

Referring next to FIG. 11 a valve system 550 can be incorporated between fluid bag 500 and syringe barrel 100 as illustrated. Such valve system can be advantageous when three or more medicants or diluents are to be mixed. Valve device 550 is depicted to have a three way conduit and a three way valve 552 controlling the flow between the adjoining conduits. Alternative valve systems are contemplated.

Utilizing the illustrated valve configuration, a first diluent or medicant component can be provided in fluid bag 500, a second component or diluent can be provided in syringe barrel 100 and a third component can be provided in medicant vial 400. If additional components are to be added, such can be achieved utilizing conduit 558 and appropriate positioning of valve 552. As depicted, valve device 550 can comprise removable fixtures for reversible attachment of syringe barrel 100 at outlet 554 and syringe and fluid bag 500 at outlet 556. Mixing and administration of the components can be achieved by appropriate positioning of valve 552.

In one aspect, the invention pertains to packaging configurations for protecting a syringe from becoming contaminated and/or for protecting the administrating person or handler from exposure to the contents of the syringe device. Protection of the administrating personnel and other device handlers becomes important when administrating or handling agents that may contain one or more potentially dangerous material such as components that may be allergens, teratagens, endocrine-disrupters, carcinogens or otherwise toxic or potentially toxic materials. The described configurations below may be utilized with the devices described herein, with devices described in the earlier filed applications that are incorporated by reference, or with conventional syringe devices and components thereof.

Referring to FIG. 12, protective packaging in accordance with the invention will typically encase the entire mixing/administration system including all components of the structure. The packaging may be loose, with excess room in its confines to allow manipulation of the device to prepare a medicant for administration such as depicted. Methodology for manipulation of the various mixing devices is analogous to that described above. As depicted in FIG. 12 a protective packaging 600 is shown to completely encase the syringe device from FIG. 1 shown in an initial "pre-mixed" configuration. In the depicted embodiment packaging 600 is relatively loose and is formed to generally mimic the overall shape of the mixing/administration system. In this case packaging is tubular and tapered to generally conform to the shape of the device. Alternatively, the shape may be rectangular, sleeve-like, pouch-like, or sack-like.

Packaging 600 forms an internal compartment 610. In preferred embodiments the packaging of the invention provides a sterile internal environment to protect the device and its content from contamination. Sterilization may occur during and/or after sealing of the packaging. Terminal sterilization may be performed which can provide a final sterilization of all components (packaging and enclosed device). Terminal sterilization may involve sterilization during or after the sealing process utilizing one or more sterilization techniques including, but not limited to exposure to vaporized $H_2O_2$, gamma rays, electron beam irradiation, chemiclave (e.g. trace formaldehyde), autoclave (e.g. at a temperature of at least 121° C. for at least 21 minutes at an appropriate pressure as would be understood by one skilled in the art), etc. The method(s) utilized for terminal sterilization may depend upon the materials of the device components, drug components, the liquids present, if any, and/or the packaging materials.

Packaging 600 is preferably provided such that mixing can be completed without opening or puncturing of the packaging. Perforation 602 or a removable tear strip or other access can be provided preferably at the forward end of syringe barrel 100 to allow access to the device for administration purpose while minimizing exposure to the device contents. Such positioning can also minimize the portion of the device which is exposed to the external atmosphere. Alternatively, a perforation line or point can be provided which can be torn or otherwise penetrated by the needle cover. The packaging can then be pulled back slightly to expose the needle cover and allow administration to be performed while minimizing exposure to the device.

The protective packaging of the invention is not limited to any particular material. The packaging can be formed of a single material or from two or more materials. Referring to FIG. 13 packaging material 600 in certain aspects can be a laminate material comprising two or more layers of differing materials 604, 606, 608 for example. Material 600 will have an outer surface 603 and an inner surface 609 which will face the syringe device. Alternatively or additionally, packaging material 600 can comprise a composite material. Various coating materials may also be utilized. In particular preferred aspects, the packaging comprises a translucent or transparent plastic film of one or more materials that allows the device to be visible for the mixing and/or administration process. It can also be preferable that the film provides protection from UV rays. The packaging material may also be provided to provide evaporation protection and in particular instances to provide an $O_2$ barrier. Where the material utilized provides an $O_2$ barrier, the packaging may be filled such that interior compartment 610 comprises nitrogen or other inert gas. In particular embodiments, the packaging can be multilayered to provide multiple of these protective functions.

Example materials which may be utilized for packaging include, but are not limited to polypropylene (PP), polyvinyls, aluminum foil, aluminum oxide coated nylon, biaxially oriented (biax) nylon (BO nylon), biax polyethylene terephthalate (BOPET), aluminum oxide coated BOPET, polycarbonate, oriented polypropylene (OPP), biax OPP (BOPP), high density polyethylene (HDPE), medium density polyethylene (MDPE), low density polyethylene (LDPE), linear low density polyethylene (LLDPE), ethylene vinyl acetate copolymer (EVA), metallocene, ionomer, polyvinylidene chloride (PVdC), metallized PET, metallized OPP, poly(ethylene vinyl alcohol) (EVOH), coex, surlyn, silicon oxide coated BOPET, paper and/or coated or uncoated TYVEK® (E. I. du Pont de Nemours and Company, Wilmington Del.). The materials utilized can depend upon the protections desired and the method of sterilization to be utilized.

It is to be understood that the packaging concepts of the invention are not limited to the devices specifically described herein or in the earlier filed applications. For example, the packaging of the invention can be used in conjunction with conventional syringes, conventional syringe systems, conventional mixing systems, conventional medicant delivery components and systems, devices and components yet to be developed.

Figure 14:
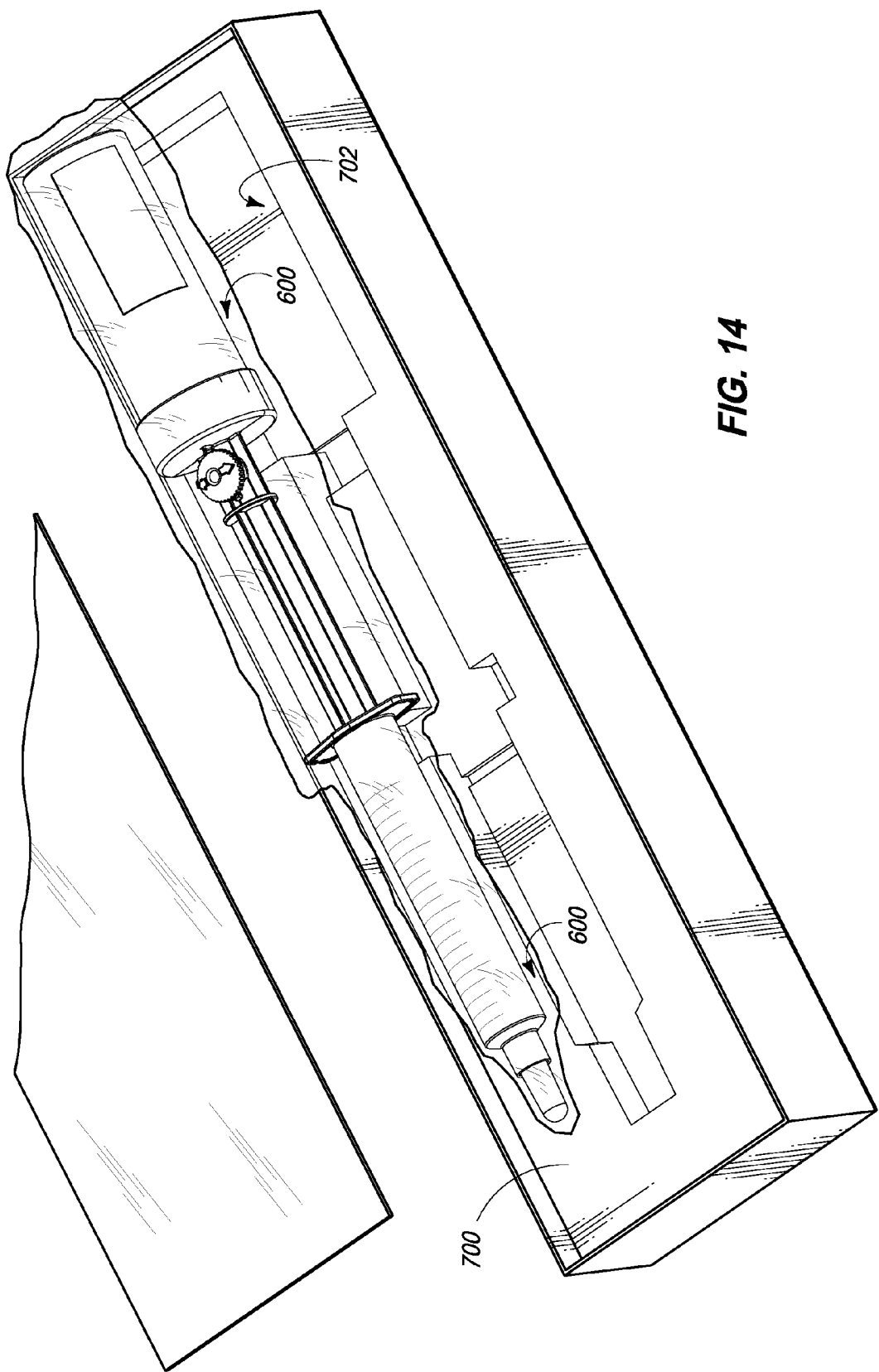
FIG. 14 illustrates an additional aspect of protective packaging in accordance with one aspect of the invention.

Referring next to FIG. 14, the protective packaging encased syringe system of FIG. 13 can be further packaged within a tray 700 which can comprise a shaped cavity 702. Preferably, shaped cavity 702 is shaped to mimic the overall contours of the device in an initial configuration (pre-mixed). Such cavity shaping can assist in supporting the device and can further stabilize the device in an initial configuration to prevent sliding of the piston within the syringe barrel during shipment, storage and handling. Tray 700 can include a cover with appropriate labeling.

Figure 15:
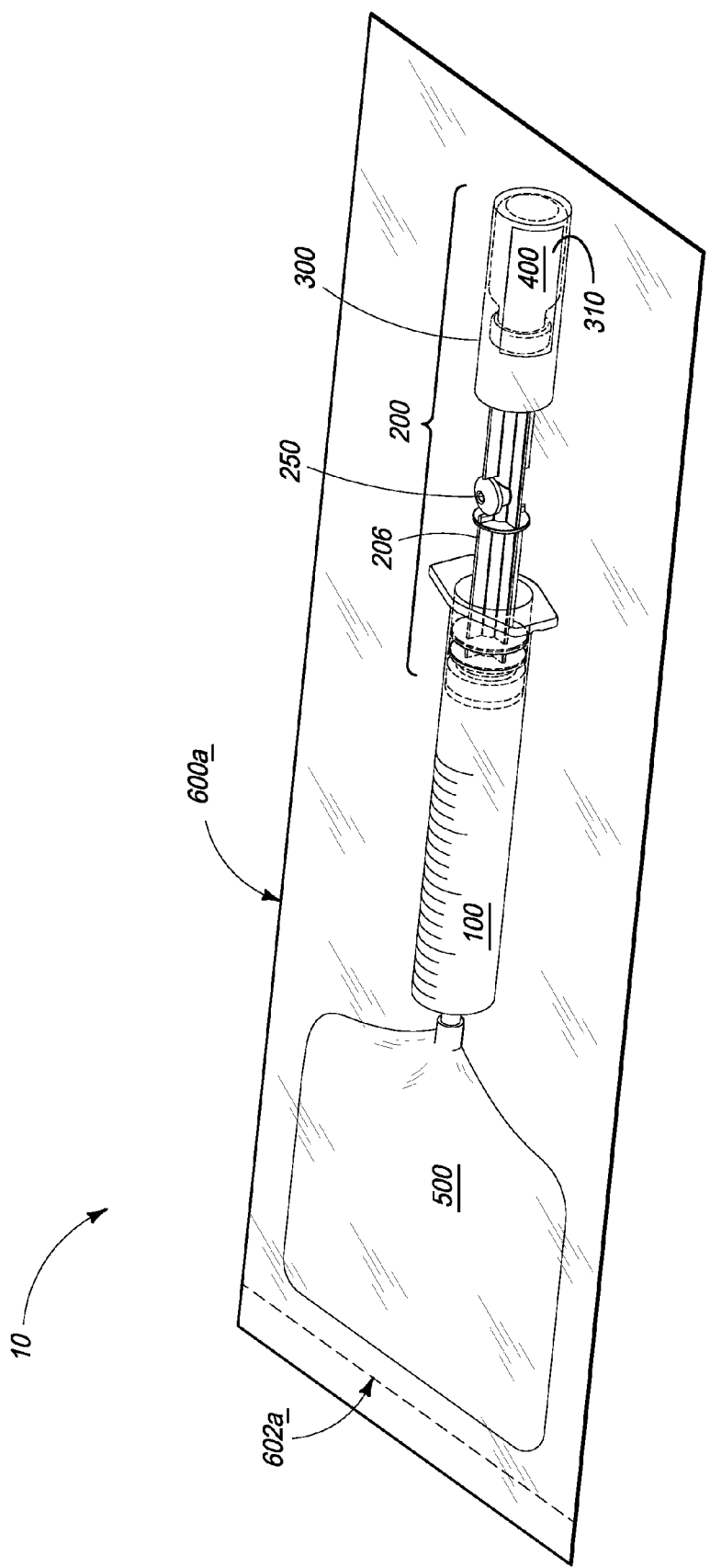
FIG. 15 illustrates an alternative mixing/administration system including protective packaging in accordance with another aspect of the invention.

Additional packaging is shown in FIG. 15. Such illustrates a bag-like or pouch-like packaging configuration 600a which encases an entire syringe device including the barrel component 100, piston component 200 and a fluid bag component 500. Packaging 600a can be evacuated or can have air, nitrogen or other inert gas within its confines. Preferably, packaging 600a is flexible enough to allow mixing of medicant components without exposing the device to an external environment or without exposing handlers to the components of the device. Once mixing has occurred, access to the device can be gained by a tear strip or perforation 602a.

Figure 16:
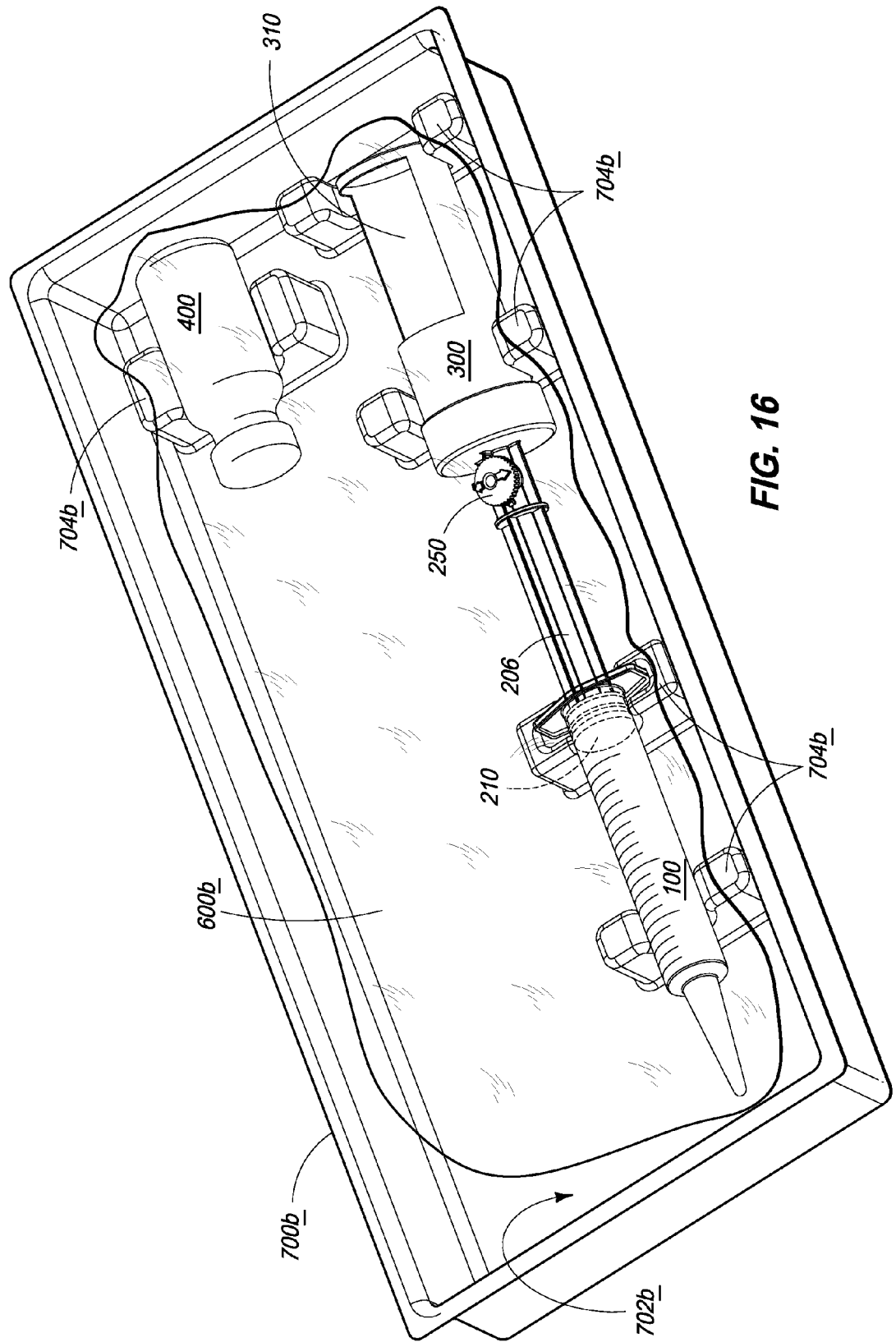
FIG. 16 illustrates another alternative mixing administration system including protective packaging in accordance with another aspect of the invention.

In particular systems a vial or container containing a medicant can be provided separately from the remaining components of the mixing administration device but can be packaged within the same protective packaging as illustrated in FIG. 16. As shown, a protective packaging 600b encases a mixing administration system comprising a syringe barrel 100 and a syringe piston 200 with the housing configured to receive a vial through an opening 310. However, vial 400 is provided separately, but is encased within the same protective packaging 600b. Packaging 600b can preferably be bag or pouch-like and can either be evacuated or can contain air, nitrogen or other inert gas. Packaging can further include a tray 700b having a cavity 702b. Tray 700b can further include raised protrusions 704b for supporting the syringe device and the vial. Protrusions 704b proximate vial 400 preferably extend beyond the maximum diameter of vial 400 to protect the vial during handling, shipping and storage. The protruding portions are preferably shaped to conform to the shape of the vial and syringe devices to provide support and maintain an initial position of the syringe device.

Figure 17:
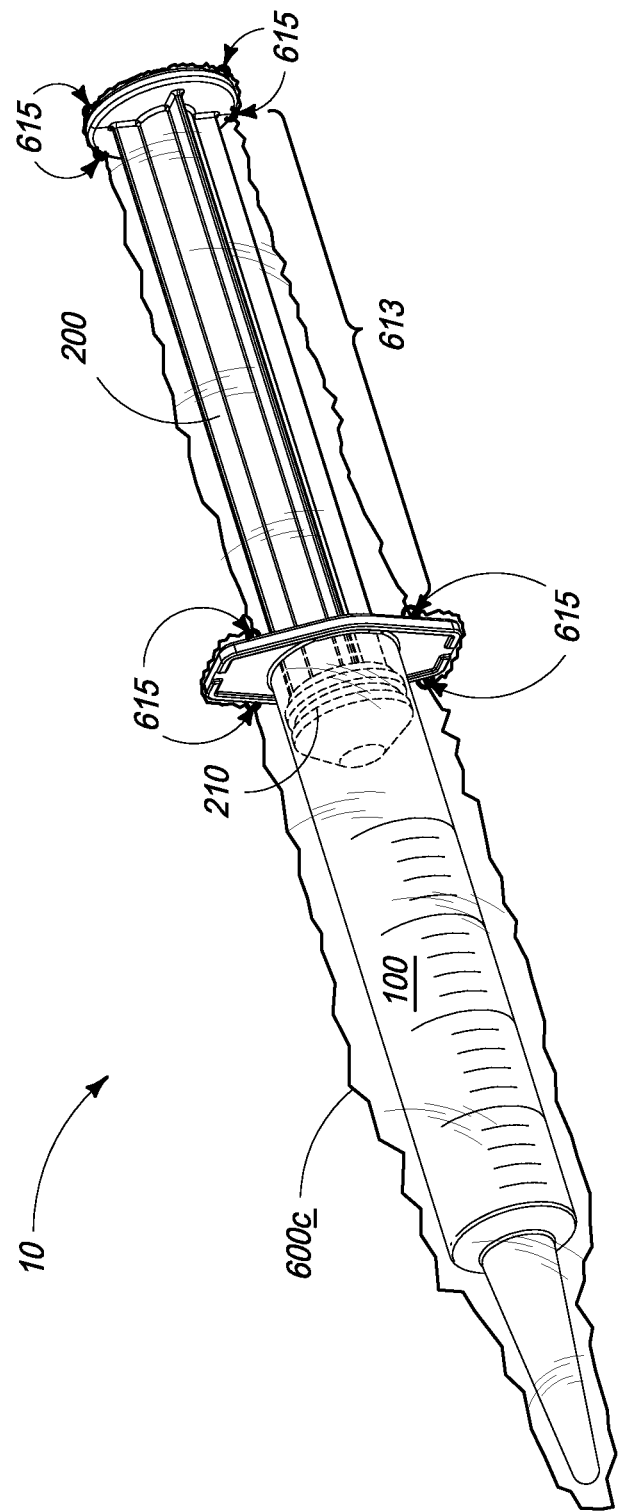
FIG. 17 illustrates a syringe device having protective packaging in accordance with another aspect of the invention.
Figure 18A:
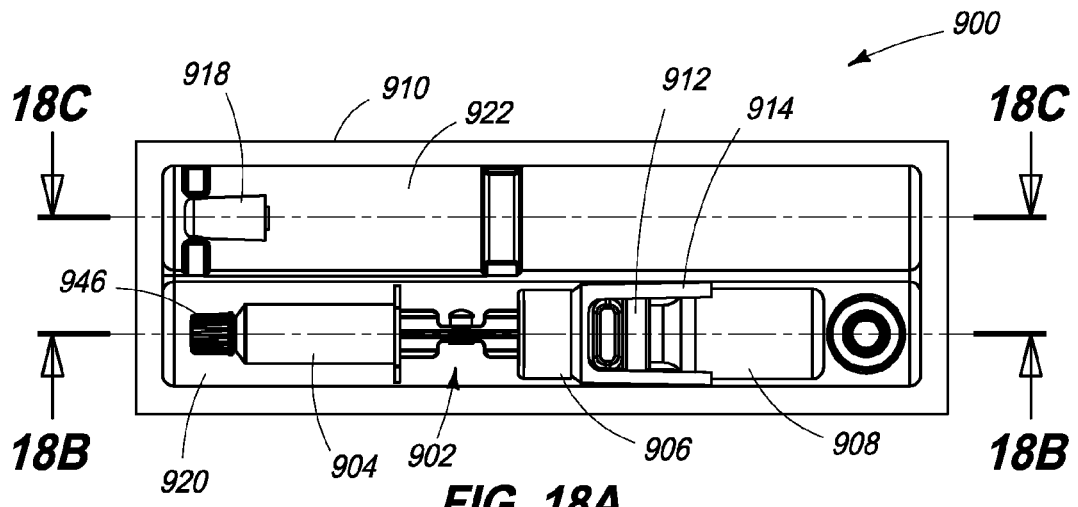
FIG. 18A illustrates a mixing/administration assembly, with FIG. 18B illustrating the assembly in one cross section and FIG. 18C illustrating the assembly in another cross section according to an embodiment of the disclosure.
Figure 18B:
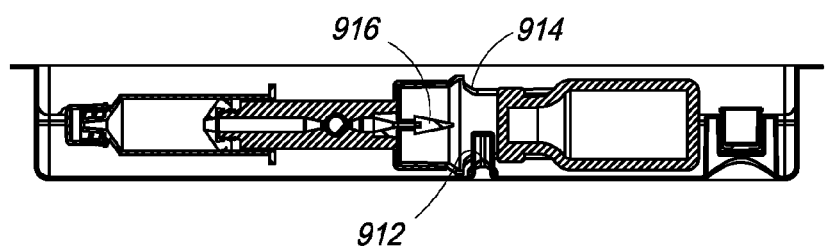
Figure 18C:
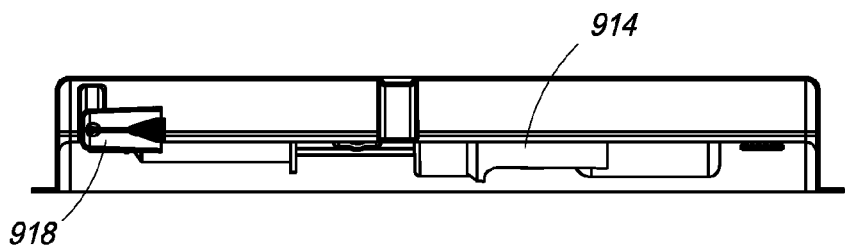

With reference to FIG. 17, another aspect of packaging in accordance with the invention is illustrated. In the depicted embodiment packaging 600c is shown to conform to the shape or package contents. Here a conventional syringe is used to illustrate the packaging concept. This fully conforming packaging can also be used with the syringe mixing administration devices discussed above and those disclosed in the earlier filed applications which are incorporated herein by reference. Packaging 600c can preferably be flexible and tear resistant and can be heat sealed to the body of the device within. The packaging may optionally include one or more rigid and/or semi-rigid components 613 which can support or stabilize one or more devices structures or positioning of device features relative to another. For example, in the depiction in FIG. 17 rigid or semi-rigid packaging 613 can be utilized over the piston stem area to prevent piston 200 from inserting within syringe barrel 100. Such support features may also help minimize or prevent damage from impact that may occur, for example, during shipping. For unitary device configurations such as those discussed above, such packaging can preferably be flexible enough to allow for manipulation of the device within the packaging.

Additionally or alternatively, packaging can be attached to the device at one or more points 615. Such attachment can be achieved utilizing, for example, heat sealing, welding, ultrasonic methods or adhesives. The points of attachment are not limited to any particular location or number. Preferably, the attachments stabilize the positioning of the device during shipping and storage and can be disconnected from the device by pulling away of the packaging from the device by the user for manipulation during preparation for administration.

Referring to FIGS. 18-24 additional medicant mixing/administration systems 900 and methods of using same are provided. Referring to FIGS. 18A-C system 900 can include a protective material 910 that at least partially encompasses syringe assembly 902. Syringe assembly 902 can have a barrel 904 as well as a piston 906. Material 910 can be configured to support syringe assembly 902.

A member 912 can be included in the system. Member 912 can separate piston 906 from vial 908, for example. Protective material 910 can be a tray configured to support both syringe assembly 902 and medicant vial 908. In accordance with example implementations, member 915 can be coupled to and/or extend from the tray. Accordingly, the tray can be molded and member 912 can be molded as part of the tray.

In accordance with example implementations, syringe piston 906 can be configured to couple to medicant vial 908. Accordingly syringe piston 906 can include a medicant vial housing 914 extending from an end of piston 906. Vial housing can define a chamber configured to receive medicant vial 908. A vial-piercing device 916 can be coupled to syringe piston 906. Device 916 can be separated from medicant vial 908 by member 912.

In accordance with example medicant mixing/administration methods, sufficiently clearing restraining member 912 from between medicant vial 908 and syringe piston 916 can allow for the user to pierce medicant vial 908 with piercing structure 916 coupled to the syringe piston. The piercing providing medicant from the vial to syringe assembly 902. In accordance with example implementations, this can be performed within a sealed package thereby limiting contamination scenarios. Methods can also include coupling medicant vial 908 with the package to remove medical vial 908 from piercing structure 916.

Medicant mixing/administration system 900 can also include syringe assembly 902 and a needle housing 918 coupled to protective material 910. Protective material 910 can define at least two compartments 920 and 922, compartment 920 receiving syringe assembly 902. Compartment 920 can receive the assembly 902 in the extended unfilled configuration. Compartment 920 can also define member 912. Compartment 922 can include needle housing 918. These compartments can be defined as part of a tray.

The compartments can be aligned lengthwise and adjacent one another, with needle housing 918 being coupled near a terminus of compartment 912. In accordance with example implementations, both compartments can be configured to receive syringe assembly 902.

Figure 19:
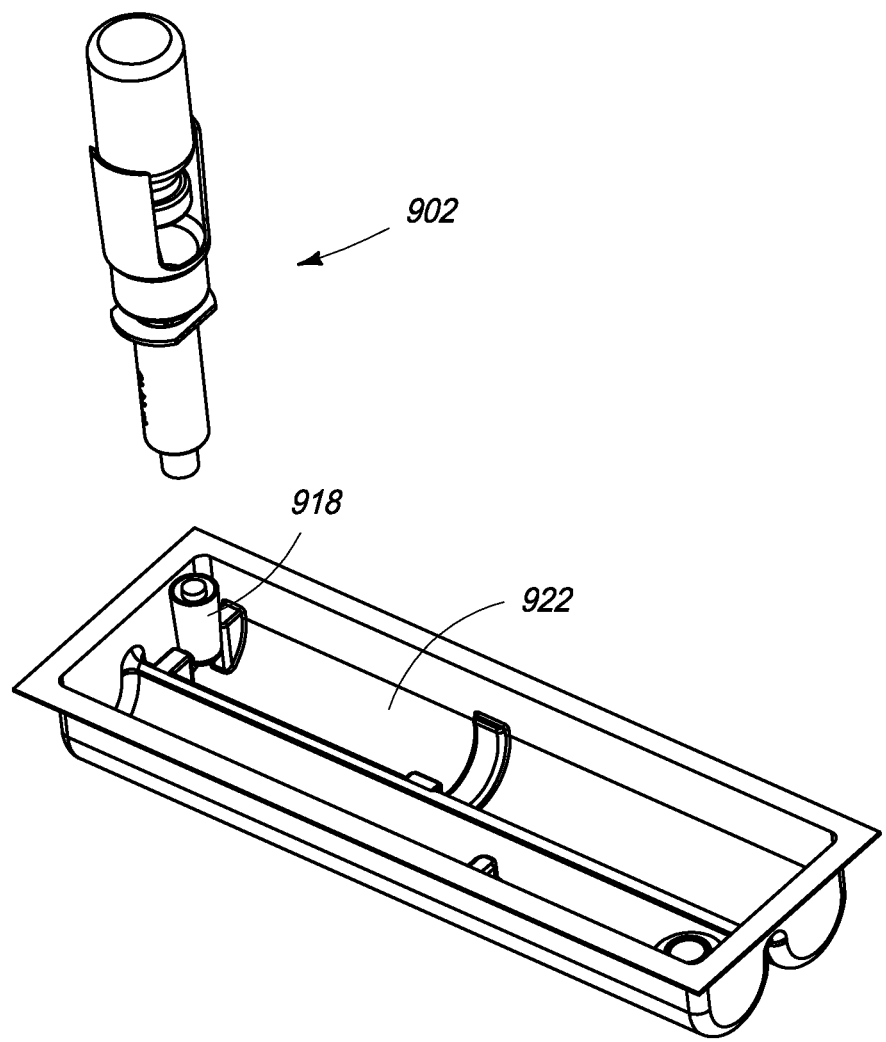
FIG. 19 illustrates a mixing/administration assembly in one configuration according to an embodiment of the disclosure.
Figure 20:
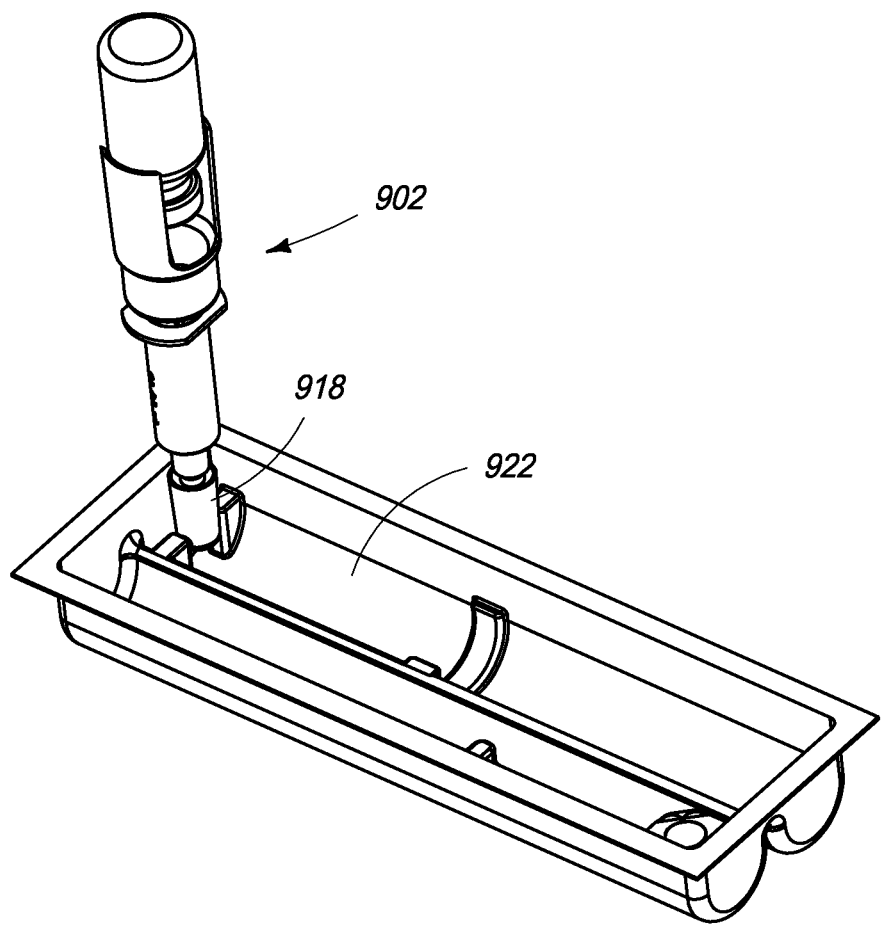
FIG. 20 illustrates a mixing/administration assembly in another configuration related to FIG. 19 according to embodiment of the disclosure.
Figure 21:
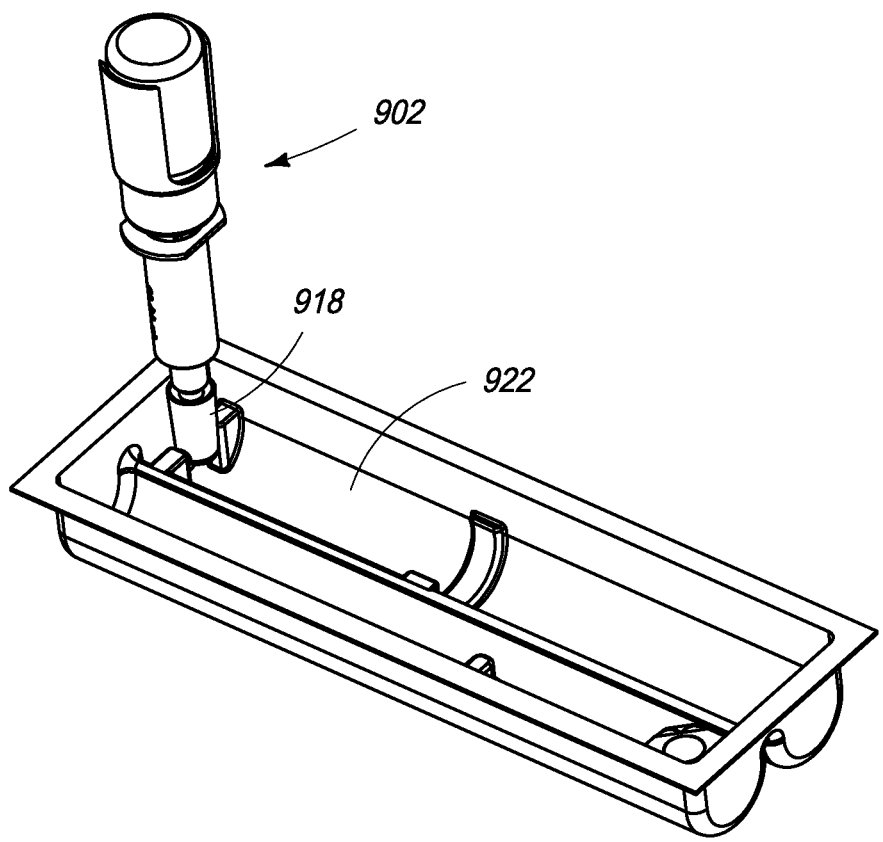
FIG. 21 illustrates a mixing/administration assembly in another configuration related to FIGS. 19 and 20 according to embodiment of the disclosure.
Figure 22:
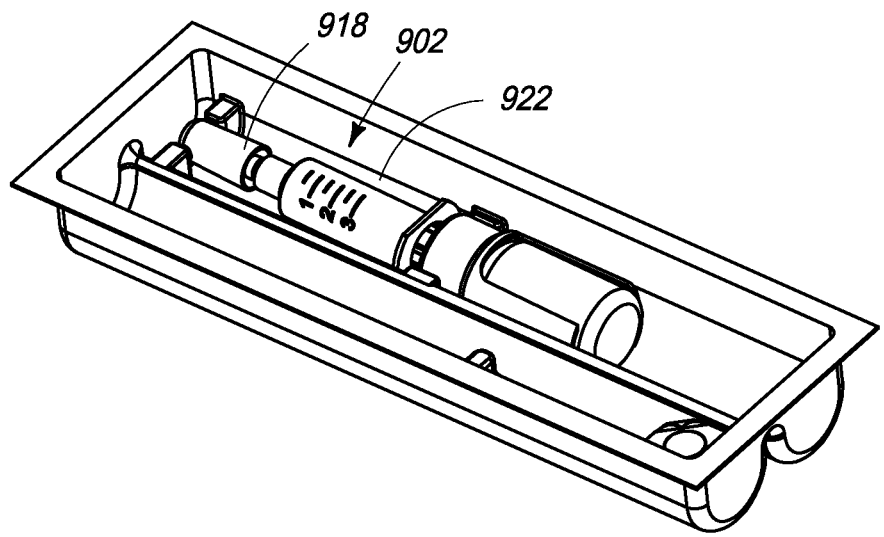
FIG. 22 illustrates a mixing/administration assembly in another configuration related to FIGS. 19-21 according to embodiment of the disclosure.
Figure 23:
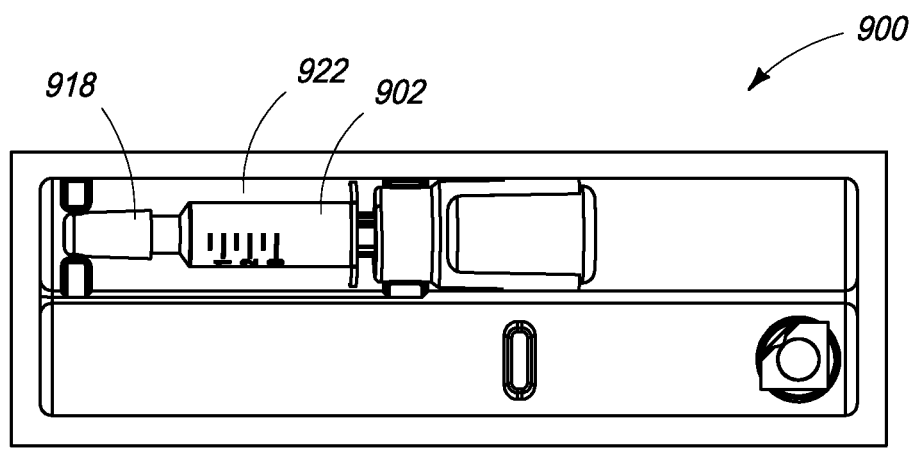
FIG. 23 illustrates a mixing/administration assembly in another configuration related to FIGS. 19-22 according to embodiment of the disclosure.
Figure 24A:
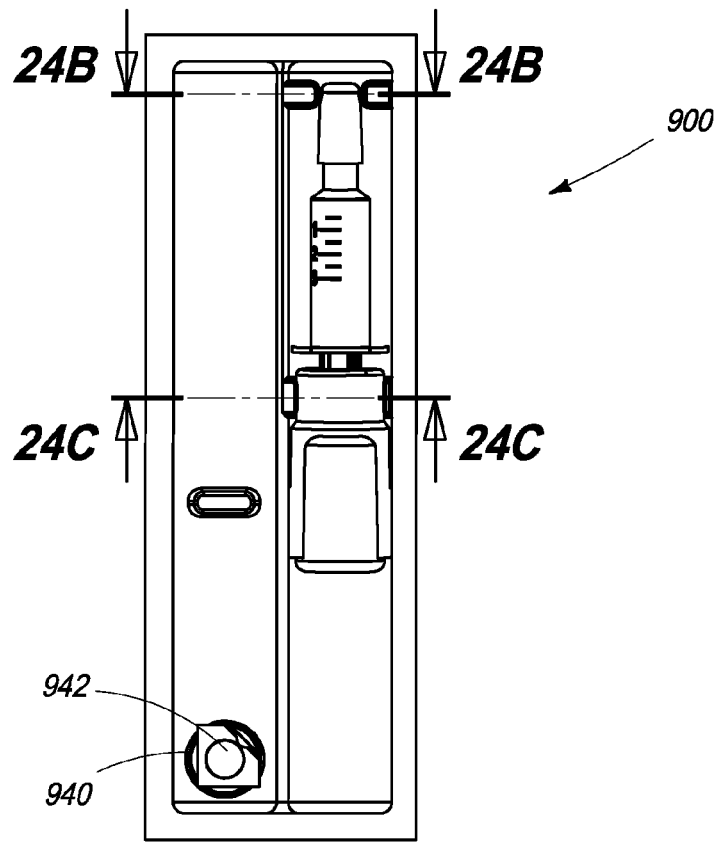
FIG. 24A illustrates a mixing/administration assembly in another configuration related to FIGS. 19-23, with FIG. 24B illustrating the assembly in one cross section and FIG. 24C illustrating the assembly in another cross section according to embodiment of the disclosure.
Figure 24B:
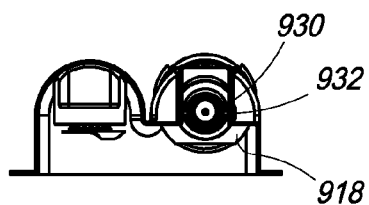
Figure 24C:
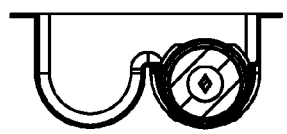

Needle housing 918 can be rotatable between at least two positions, a first position aligned lengthwise with the length of the protective material as shown in FIG. 18 and a second position substantially normal to the first position as shown in FIGS. 19-21. In accordance with example implementations, needle housing 918 can be biased in the second position as shown in FIGS. 19-21. Packaging provided to encompass housing 918 can restrain housing 918 against this bias in the first position. Upon removal of packaging, housing 918 can rotate to the second position.

Accordingly a medicant mixing/administration method can include upon opening a package containing a syringe assembly, extending the needle housing from the package. A user can then couple a needle within the needle housing to the syringe assembly as shown in FIGS. 19-23. In accordance with other example implementations, the needle within the needle housing can be withdrawn. Assembly 902 can be coupled to compartment 922 for eventual disposal maintaining the needle protected within housing 918. Accordingly, the systems and/or methods of the present disclosure provide enhanced safety when handling syringes, particularly syringes having needles attached thereto as the entire package including the assembly engaged with the package can be discarded protecting disposal workers from injury when handling medical waste for example.

In accordance with additional embodiments, the systems and methods can include "cap technology" consistent with that described in U.S. Pat. No. 8,162,899 issued Apr. 24, 2012; U.S. patent application Ser. No. 13/688,044 filed Nov. 28, 2012; and U.S. patent application Ser. No. 13/688,078 filed Nov. 28, 2012; the entirety of each of which are hereby incorporated herein by reference. Accordingly, system 900 can include at least two caps, cap 942 received with cap recess 940 as well as cap 946 coupled to assembly 902. These caps can be configured and used in accordance with the above referenced materials, the entirety of each of which is incorporated by reference herein.

The mixing/administration systems of the invention can be used with ease by a variety of personnel including, for example, home care providers, battlefield or disaster relief workers, or by patients themselves with minimal risk of error or contamination. In particular embodiments, devices of the invention are provided in protective packaging that decreases the likelihood of exposure of personnel to the contents of the device. The packaging is provided to meet or exceed standards for cleanliness and sterility as documented in U.S. Pharmacopia §797.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A medicant mixing/administration system comprising:
   a syringe assembly comprising a syringe barrel and a syringe piston, wherein the piston defines a housing configured to receive a medicant vial;
   a medicant vial extending partially into the housing to define a space between the medicant vial and the piston;
   a protective material supporting the syringe assembly and medicant vial;
   a member defined by the protective material, the member extending into the housing and between the piston and medicant vial, separating the piston of the syringe assembly from the medicant vial when the assembly and vial are supported by the protective material; and
   a recess defined by the protective material, the recess configured to receive and support an uncoupled cap.

2. The system of claim 1 wherein the protective material is a tray configured to support both the syringe assembly and the medicant vial.

3. The system of claim 2 wherein the housing defines openings through which the member extends when the assembly and vial are supported by the protective material.

4. The system of claim 3 wherein the plunger defines a fluid conduit extending to the housing.

5. The system of claim 1 wherein the assembly further comprises a vial-piercing member extending from the piston and to within the housing.

6. The system of claim 5 wherein the member separates the vial from the vial-piercing member when the assembly and vial are supported by the protective material.

7. The system of claim 5 wherein the medicant vial further comprises septum configured to be pierced by the vial-piercing member.

* * * * *

UNITED STATES PATENT AND TRADEMARK OFFICE
CERTIFICATE OF CORRECTION

| | | |
|---|---|---|
| PATENT NO. | : 9,522,097 B2 | Page 1 of 1 |
| APPLICATION NO. | : 13/838530 | |
| DATED | : December 20, 2016 | |
| INVENTOR(S) | : Patrick O. Tennican et al. | |

It is certified that error appears in the above-identified patent and that said Letters Patent is hereby corrected as shown below:

On the Title Page

(56) References Cited – Replace "2,693,186 A   11/1954 Ricker et al." with --2,693,186 A   11/1954 Riker et al.--

(56) References Cited – Replace "7,134,974 B2   11/2006 Almasian et al." with --7,137,974 B2   11/2006 Almasian et al.--

(56) References Cited – Replace "JP     3009662       1/1995" with --JP     3009662     2/1995--

(56) References Cited – Replace "Clip'n Ject, [retrieved online Nov. 9, 2005]: http://www.westpharma.comiproducts/clip_n__Ject. asp?1=0" with --Clip'n Ject, [retrieved online Nov. 9, 2005]: http://www.westpharma.com/products/clip_n_Ject. asp?1=0--

In the Specification

Column 8, Line 35 – Replace "prior of insertion" with --prior to insertion--

Signed and Sealed this
Ninth Day of May, 2017

Michelle K. Lee
*Director of the United States Patent and Trademark Office*